(12) United States Patent
Cai et al.

(10) Patent No.: US 11,479,603 B2
(45) Date of Patent: Oct. 25, 2022

(54) POLYPEPTIDE AND ANTIBODY BOUND TO POLYPEPTIDE

(71) Applicant: SHANGHAI YILE BIOTECHNOLOGY CO., LTD., Shanghai (CN)

(72) Inventors: Xiumei Cai, Shanghai (CN); Ruping Dai, Shanghai (CN); Huamao Wang, Shanghai (CN)

(73) Assignee: SHANGHAI YILE BIOTECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 16/643,411

(22) PCT Filed: Aug. 28, 2018

(86) PCT No.: PCT/CN2018/102745
§ 371 (c)(1),
(2) Date: Feb. 28, 2020

(87) PCT Pub. No.: WO2019/042282
PCT Pub. Date: Mar. 7, 2019

(65) Prior Publication Data
US 2021/0061896 A1    Mar. 4, 2021

(30) Foreign Application Priority Data

Aug. 28, 2017 (CN) .......................... 201710752743.8

(51) Int. Cl.
| | | |
|---|---|---|
| *C07K 16/22* | (2006.01) | |
| *A61P 37/06* | (2006.01) | |
| *A61P 25/00* | (2006.01) | |
| *C07K 14/48* | (2006.01) | |
| *C12N 15/10* | (2006.01) | |
| *A61K 39/00* | (2006.01) | |

(52) U.S. Cl.
CPC .............. *C07K 16/22* (2013.01); *A61P 25/00* (2018.01); *A61P 37/06* (2018.01); *C07K 14/48* (2013.01); *C12N 15/1037* (2013.01); *A61K 2039/505* (2013.01); *C07K 2317/33* (2013.01); *C07K 2317/622* (2013.01); *C07K 2317/92* (2013.01)

(58) Field of Classification Search
CPC ................ C07K 16/22; C07K 2317/33; C07K 2317/622; C07K 2317/92; A61K 2039/505; A61P 25/00; A61P 37/06
See application file for complete search history.

(56) References Cited

FOREIGN PATENT DOCUMENTS

| | | |
|---|---|---|
| CN | 1052142 A | 6/1991 |
| CN | 101060863 A | 10/2007 |
| CN | 101360759 A | 2/2009 |
| CN | 103638521 A | 3/2014 |
| CN | 105770889 A | 7/2016 |
| WO | 2017032293 A1 | 3/2017 |

OTHER PUBLICATIONS

International Search Report (in English and Chinese) and Written Opinion issued in PCT/CN2018/102745, dated Nov. 22, 2018.
Wetmore et al., "Brain-derived neurotrophic factor (BDNF) peptide antibodies: characterization using a Vaccinia virus expression system", Journal of Histochemistry & Cytochemistry, 41 (4), pp. 521-533, Apr. 1993, Cited in International Search Report.
Su et al., "Preparation and identification of monoclonal antibodies against human brain-derived neurotrophic factor", J First Mil Med Univ, 22 (10), Oct. 30, 2002, total 4 pages provided; with English translation of the Abstract, Cited in International Search Report.
Yang et al., "Effects of BDNF antibody block on IL-6 expression in lung of rats subjected to brain ischemia", J Sichuan Univ (Med Sci Edi); 43 (6), 2012, 6 pages provided; with English translation of the Abstract, Cited in International Search Report.

*Primary Examiner* — Kimberly Ballard
(74) *Attorney, Agent, or Firm* — Hamre, Schumann, Mueller & Larson, P.C.

(57) ABSTRACT

An antibody for being specifically bound to a pro brain-derived neurotrophic factor (pro-BDNF) and a bound epitope. The antibody and the protein are used for treating autoimmune diseases. By inhibiting the activity induced by the pro-BDNF, rheumatoid arthritis, psoriasis, systemic lupus erythematosus, lupus nephriti, chronic obstructive pulmonary diseases, asthma or cystic fibrosis, multiple sclerosis and other autoimmune diseases are treated.

5 Claims, 6 Drawing Sheets
Specification includes a Sequence Listing.

POLYPEPTIDE AND ANTIBODY BOUND TO POLYPEPTIDE

TECHNICAL FIELD

The invention relates to the field of biomedicine. In particular, the invention relates to a polypeptide fragment of pro-BDNF and a protein binding to the polypeptide fragment, and also relates to the use of the polypeptide fragment of pro-BDNF.

BACKGROUND

Autoimmune disease (AID) is a type of disease, in which autoimmune tolerance is broken, and the immune system is activated to attack autoantigens, so as to cause damage to tissues and organs. The etiology and pathogenesis of autoimmune disease are unclear, and it is currently considered to be a hypersensitive reactive disease against autoantigen caused by autoantibodies, autoreactive T lymphocytes, or both. There are no curative medicines in clinical practice. The timely application of traditional glucocorticoids and immunosuppressants can control the disease and improve the survival rate of patients. However, long-term use of them will lead to a series of side effects. In severe cases, the quality of life of patients will be affected, or even their lives will be threatened. Moreover, some patients are not sensitive to glucocorticoid and immunosuppressive therapy.

In recent years, new treatment strategies have been proposed with the deep understanding of the molecular mechanism of AID, including gene therapy, epigenetic intervention, small molecule Toll-like receptor inhibitors, anti-inflammatory factor antibodies, backfusion of stem cells and regulatory T cell autolog, dendritic cell vaccine, etc. Some of these therapeutic drugs or methods have been used in clinic, and some are still in the clinical research stage (such as stem cell autotransfusion therapy, etc.) and even animal experimental stages (such as epigenetic regulation, etc.).

However, these drugs cannot replace glucocorticoids as first-line drugs, therefore, there is an urgent need for new, safe and effective therapeutic drugs and methods for clinical application.

SUMMARY OF THE INVENTION

An object of the present invention is to provide a polypeptide, by which an antibody that specifically binds to the polypeptide can be obtained; and the antibody can be effectively used for the treatment of autoimmune diseases.

In the first aspect, the present invention provides a polypeptide comprising an amino acid sequence as shown in SEQ ID NO: 41.

In a preferred embodiment, the amino acid sequence of the polypeptide is shown in SEQ ID NO: 41.

In the second aspect, the present invention provides a polypeptide comprising an amino acid sequence shown in SEQ ID NO: 44.

In a preferred embodiment, the amino acid sequence of the polypeptide is shown in SEQ ID NO: 44.

In the third aspect, the present invention provides a polypeptide comprising an amino acid sequence as shown in SEQ ID NO: 47.

In a preferred embodiment, the amino acid sequence of the polypeptide is shown in SEQ ID NO: 47.

In a specific embodiment, the present invention provides a polynucleotide encoding a polypeptide according to any one of the first to third aspects of the present invention.

In a specific embodiment, the present invention provides an expression vector comprising the encoding polynucleotide of the present invention.

In a specific embodiment, the present invention provides the use of the polypeptide according to any one of the first to third aspects of the present invention in screening or preparing a specific antibody thereof.

In the fourth aspect, the invention provides a protein that specifically binds to the polypeptide of any one of the first to third aspects of the invention.

In a specific embodiment, the binding affinity of the protein to human pro-BDNF is <10 nM.

In a specific embodiment, the protein is an antibody.

In a preferred embodiment, the antibody is a monoclonal antibody, a polyclonal antibody, or an antibody fragment.

In a preferred embodiment, the antibody may be selected from a chimeric antibody, a humanized antibody, or a fully human antibody.

In a specific embodiment, the light chain variable region of the antibody has:
CDR1 as shown in SEQ ID NO: 4 or SEQ ID NO: 14;
CDR2 as shown in SEQ ID NO: 5 or SEQ ID NO: 15; and
CDR3 as shown in SEQ ID NO: 6 or SEQ ID NO: 16.

In a specific embodiment, the light chain variable region of the antibody has:
CDR1 as shown in SEQ ID NO: 4; CDR2 as shown in SEQ ID NO: 5; and CDR3 as shown in SEQ ID NO: 6; or
CDR1 as shown in SEQ ID NO: 14, CDR2 as shown in SEQ ID NO: 15 and CDR3 as shown in SEQ ID NO: 16.

In a specific embodiment, the heavy chain variable region of the antibody has:
CDR1 as shown in SEQ ID NO: 1 or SEQ ID NO: 11;
CDR2 as shown in SEQ ID NO: 2 or SEQ ID NO: 12; and
CDR3 as shown in SEQ ID NO: 3 or SEQ ID NO: 13.

In a specific embodiment, the heavy chain variable region of the antibody has:
CDR1 as shown in SEQ ID NO: 1, CDR2 as shown in SEQ ID NO: 2 and CDR3 as shown in SEQ ID NO: 3; or
CDR1 as shown in SEQ ID NO: 11, CDR2 as shown in SEQ ID NO: 12 and CDR3 as shown in SEQ ID NO: 13.

In a specific embodiment, the antibody is selected from:
Antibody (a): the heavy chain variable region comprises the sequences as shown in SEQ ID NO: 1, SEQ ID NO: 2 and SEQ ID NO: 3, and the light chain variable region comprises the sequence shown in SEQ ID NO: 4, SEQ ID NO: 5 and SEQ ID NO: 6;
Antibody (b): the heavy chain variable region comprises the sequences as shown in SEQ ID NO: 11, SEQ ID NO: 12 and SEQ ID NO: 13, and the light chain variable region comprises the sequence as shown in SEQ ID NO: 14, SEQ ID NO: 15 and SEQ ID NO: 16;
Antibody (c): a variant of antibody (a) or antibody (b), which has or substantially has the activity of antibody (a) or antibody (b).

In a preferred embodiment, the antibody (c) is obtained by addition, deletion or substitution (preferably substitution) of one or more, for example, 1-3, preferably 1 amino acid in the sequence as shown in SEQ ID NO: 1, SEQ ID NO: 2, SEQ ID NO: 3, SEQ ID NO: 4, SEQ ID NO: 5 or SEQ ID NO: 6 of the antibody (a), and has or substantially has the activity of the antibody (a); or
the antibody (c) is obtained by the addition, deletion, or substitution (preferably substitution) of one or more, for example, 1-3, preferably 1 amino acid in the sequence as shown in SEQ ID NO: 11, SEQ ID NO: 12, SEQ ID NO: 13, SEQ ID NO: 14, SEQ ID NO: 15, SEQ ID NO: 16 of antibody (b), and has or substantially has the activity of antibody (b).

In a preferred embodiment, the amino acid substitution is a conservative amino acid substitution.

In a specific embodiment, the antibody is selected from:

Antibody (d): having a heavy chain variable region as shown in SEQ ID NO: 7 and a light chain variable region as shown in SEQ ID NO: 8;

Antibody (e): having a heavy chain variable region as shown in SEQ ID NO: 17 and a light chain variable region as shown in SEQ ID NO: 18;

Antibody (f): a variant of antibody (d) or antibody (e), which has or substantially has the activity of antibody (d) or antibody (e).

In a preferred embodiment, the antibody (f) is obtained by the addition, deletion, or substitution (preferably substitution) of one or more, for example, 1-10, preferably 1-6, more preferably 1-3, most preferably 1 amino acid in the sequence as shown in SEQ ID NO: 7 or SEQ ID NO: 8 of antibody (f), and has or substantially has the activity of antibody (f); or the antibody (f) is obtained by the addition, deletion, or substitution (preferably substitution) of one or more, for example, 1-10, preferably 1-6, more preferably 1-3, most preferably 1 amino acid in the sequence as shown in SEQ ID NO: 17 or SEQ ID NO: 18 of antibody (e), and has or substantially has the activity of antibody (e).

In a preferred embodiment, the antibody has one or more of the following characteristics:

i) binding pro-BDNF polypeptide with a $K_D$ of 10 nM or less;

ii) competitively inhibiting the binding of pro-BDNF to p75; and iii) Pro-BDNF-dependent activity.

In a specific embodiment, the protein is obtained by immunizing an animal with the polypeptide according to any one of the first to third aspects of the present invention or is obtained by screening a phage library using the polypeptide according to any one of the first to third aspects of the present invention.

In the fifth aspect, the present invention provides a pharmaceutical composition comprising the protein according to the fourth aspect of the present invention and optionally one or more pharmaceutically acceptable excipients, diluents or carrier.

In the sixth aspect, the present invention provides the use of the protein according to the fourth aspect of the present invention for preparing a medicament for the prevention, treatment or diagnosis of an autoimmune disease.

In a preferred embodiment, the autoimmune disease is a pro-BDNF-mediated autoimmune disease.

In the seventh aspect, the present invention provides the use of the protein according to the fourth aspect of the present invention for preparing a medicament for the prevention, treatment or diagnosis of a disease mediated by pro-BDNF.

In a specific embodiment, the disease is arthritis, rheumatoid arthritis, ankylosing spondylitis, aplastic anemia, psoriasis, insulin-dependent diabetes mellitus, multiple sclerosis, cryoglobulinemia, Chronic obstructive pulmonary disease, systemic lupus erythematosus (SLE), lupus nephritis, asthma, multiple sclerosis, or cystic fibrosis.

In the eighth aspect, the present invention provides the use of the protein according to the fourth aspect of the present invention for preparing a medicament for the prevention, treatment or diagnosis of a disease by inhibiting the secretion of TNF-α, IL-2, IL-6 or IL-4.

In the ninth aspect, the present invention provides the use of the protein according to the fourth aspect of the present invention for preparing a medicine for relieving pain.

In the tenth aspect, the present invention provides a nucleic acid encoding a protein according to the fourth aspect of the present invention.

In the eleventh aspect, the present invention provides a method for screening antibodies, using the polypeptide according to any one of the first to third aspects of the present invention to immunize animals or screening a phage library by using the polypeptide according to any one of the first to third aspects of the present invention.

It should be understood that, within the scope of the present invention, the technical features specifically mentioned above and below (such as in the Examples) can be combined with each other, thereby constituting a new or preferred technical solution which needs not be individually described.

MODES FOR CARRYING OUT THE INVENTION

Figure 1:
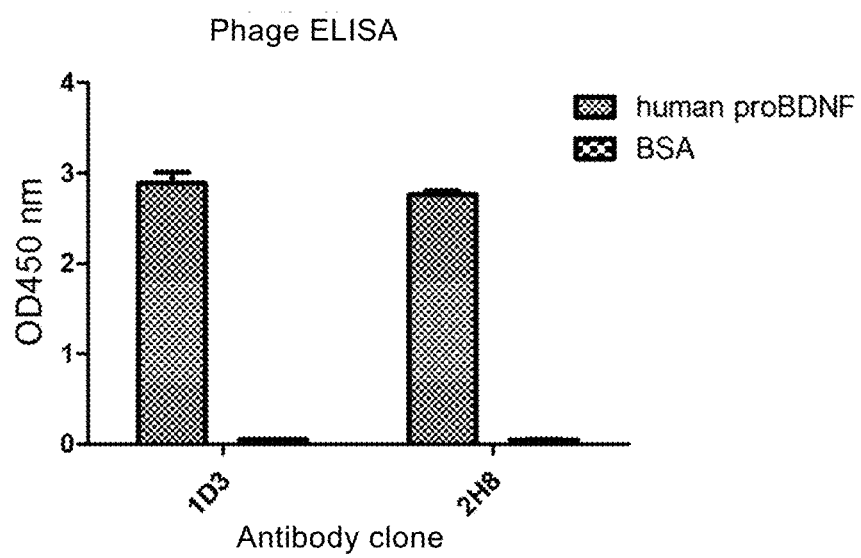
FIG. 1 is an ELISA binding diagram of the binding capabilities of 1D3 and 2H8 to human proBDNF precursor protein.

After extensive and in-depth research, the inventors unexpectedly found antibodies which can specifically bind to pro-BDNF and reduce the secretion of TNF-α, IL-2, IL-6 or IL-4 in experimental autoimmune encephalomyelitis models in vivo, and the binding epitopes of these antibodies were analyzed. The present invention was completed based on the above findings.

Terms

Scientific and technical terms used herein have the same or similar meanings as commonly understood by a skilled person in the art. Some terms are defined as follows for facilitating understanding of the present invention.

The term "proBDNF" (precursor for brain-derived neurotrophic factor) is "precursor of brain-derived neurotrophic factor", which is a precursor product of BDNF gene. Unless otherwise described, the term "pro-BDNF" refers to human pro-BDNF with the sequence as shown in SEQ ID NO: 27. In the amino acid sequence of ProBDNF molecule, the signal peptide sequence is at positions 1-18. During the secretion process, two fragments are generated at this position, among which one fragment is a polypeptide fragment containing the amino acids 19-129 of the sequence, i.e., precursor domain, named as proBDNF pro-domain, and the other fragment is the amino acid sequence at positions 130-247, i.e., the fragment encoded by the mature domain, which is processed to form a biologically active mature BDNF.

The term "p75" is a neurotrophin receptor (p75NTR), also known as CD271, and is a ligand of proBDNF.

As used herein, the term "protein of the invention" or "protein according to the invention" means a protein that binds to the polypeptide of the invention. The polypeptide of the present invention specifically refers to a polypeptide comprising the amino acid sequence as shown in SEQ ID NO: 41 or the amino acid sequence as shown in SEQ ID NO: 41; a polypeptide comprising the amino acid sequence as shown in SEQ ID NO: 44 or with the amino acid sequence as shown in SEQ ID NO: 44; or a polypeptide comprising the amino acid sequence as shown in SEQ ID NO: 47 or with the amino acid sequence as shown in SEQ ID NO: 47. Therefore, in a specific embodiment, the protein of the present invention may be an antibody or an antigen-binding portion thereof; and the protein of the present invention may also be a fusion protein comprising an antibody or an antigen-binding portion thereof.

As used herein, the term "antibody" includes a whole antibody and any antigen-binding fragments. A naturally occurring "antibody" is a glycoprotein comprising at least two heavy (H) chains and two light (L) chains connected by disulfide bond chains. Each heavy chain consists of a heavy chain variable region (abbreviated herein as VH) and a heavy chain constant region. The heavy chain constant region consists of three domains, CH1, CH2, and CH3. Each light chain consists of a light chain variable region (abbreviated herein as VL) and a light chain constant region. The light chain constant region consists of a domain CL. The VH and VL regions can be further subdivided into regions with high variability, called complementarity determining regions (CDRs), separated by relatively conservative regions, named as framework regions (FR). Each VH and VL is composed of 3 CDRs and 4 FRs arranged in the following order: FR1, CDR1, FR2, CDR2, FR3, CDR3, FR4 from the amino terminal to the carboxy terminal. The variable regions of the heavy and light chains contain a binding domain that interacts with an antigen. The constant region of an antibody can mediate the binding of immunoglobulins to host tissues or factors, including various cells of the immune system (such as effector cells) and the first component (C1q) of the classical complement system.

The terms "complementarity determining region" and "CDR" refer to a sequence of amino acids in the variable region of an antibody that confers antigen specificity and binding affinity. In general, there are three CDRs (HCDR1, HCDR2, HCDR3) in each heavy chain variable region and three CDRs (LCDR1, LCDR2, LCDR3) in the light chain variable region.

The amino acid sequence boundaries of a given CDR can be determined using a number of well-known protocols, including by Kabat et al. (1991), "Sequences of Proteins of Immunological Interest," 5th edition, Public Health Service, National Institutes of Health, Bethesda, Md. ("Kabat" numbering scheme), Al-Lazikani et al. (1997) JMB 273, 927-948 ("Chothia" numbering scheme).

As used herein, the term "antibody" refers to the full length or one or more fragments of an antibody that retains the ability to specifically bind to an antigen (e.g., part of pro-BDNF), or other polypeptides having similar antibody-binding activity. It has been shown that the antigen-binding function of an antibody can be performed by fragments of a full-length antibody. Examples included in the term "antigen-binding fragments" of antibody include Fab fragments, monovalent fragments consisting of VL, VH, CL, and CH1 domains; F(ab)2 fragments, divalent fragments comprising two Fab fragments linked by a disulfide bridge on the hinge region; Fd fragments consisting of VH and CH1 domains; Fv fragments consisting of VL and VH domains on one arm of an antibody; dAb fragments consisting of VH domains (Ward et al., 1989, Nature 341: 544-546); and an isolated complementarity determining region (CDR) or any fusion protein comprising such an antigen-binding portion.

As used herein, a "polypeptide having similar antibody-binding activity" may be a protein having an antibody-antigen binding site, such as a single domain antibody, a minibody, a dimer, a trimer, or an affinity protein with a non-antibody structure.

Although the two domains of Fv fragment, VL and VH, are encoded by separate genes, they can be joined using recombinant methods by synthesizing a linker that allows them to form a single-chain protein where the VL and VH regions are paired (scFv) (see, for example, Bird et al., 1988, Science 242: 423-426; and Huston et al., 1988, Proc. Natl. Acad. Sci. 85: 5879-5883). Such single chain antibody is also intended to be included in the term "antigen-binding fragment" of an antibody. These antibody fragments are obtained using conventional techniques known to a skilled person, and the fragments can be screened for their utility in the same manner as used for intact antibodies.

As used herein, an "isolated antibody" refers to an antibody that is substantially free of other antibodies with different antigen specificities (e.g., an isolated antibody that specifically binds pro-BDNF, such as human pro-BDNF, is substantially free of antibodies that specifically bind to antigens other than pro-BDNF). However, isolated antibodies that specifically bind pro-BDNF may have cross-reactivity with other antigens, such as pro-BDNF molecules from other species. In addition, the isolated antibodies may be substantially free of other cellular material and/or chemicals.

The term "epitope" means a protein determinant capable of specifically binding to an antibody. An epitope usually consists of a chemically active surface grouping of a molecule such as amino acid or sugar side chains, and typically has specific structural characteristics and charge characteristics.

The term "isotype" refers to a type of antibody provided by the heavy chain constant region gene (e.g., IgM, IgE, IgG, such as IgG1 or IgG4). Isotypes also include modified forms of one of these species, where modifications have been made to alter Fc function, for example to enhance or decrease effector function or binding to Fc receptors.

As used herein, the term "fully human antibody" is intended to include antibodies having variable regions in which both of the framework and CDR regions are derived from sequences of human origin. In addition, if the antibody contains a constant region, the constant region is also derived from such human sequence, such as a human germline sequence, or a human germline sequence or a mutated form of antibody comprising a consensus frame sequence derived from human framework sequence analysis (e.g., Knappik et al., 2000, J Mol Biol 296: 57-86). Fully human antibodies of the present disclosure may include amino acid residues that are not encoded by human sequences (e.g., mutations introduced by random or site-directed mutagenesis in vitro or by somatic mutations in vivo). However, as used herein, the term "fully human antibody" is not intended to include antibodies in which CDR sequences derived from the germline of another mammalian species such as a mouse have been grafted onto human framework sequences.

As used herein, the term "recombinant human antibody" includes all of human antibodies produced, expressed, produced or isolated by recombinant means, such as antibodies isolated from transgenic or transchromosomic animals (e.g., mice) of human immunoglobulin genes, or hybridomas prepared therefrom, from host cells transformed to express human antibodies, such as antibodies isolated from transfected tumors, antibodies isolated from from recombinant combinatorial human antibody libraries, and antibodies prepared, expressed, generated or isolated by any other means including splicing all or part of a human immunoglobulin gene sequence with other DNA sequences. Such recombinant human antibodies have variable regions in which both of framework and CDR regions are derived from human germline immunoglobulin sequences. However, in certain embodiments, such recombinant human antibodies can be subjected to in vitro mutagenesis (or, somatic cell mutagenesis in vivo when transgenic animals with human Ig sequences are used), therefore, the amino acid sequences of the VH and VL regions of the recombinant antibody are derived from and related to the human germline VH and VL sequences, but may not be sequences that naturally occur in the human antibody germline library in vivo.

As used herein, "isotype" refers to a type of antibody (e.g., IgM, IgE, IgG, such as IgG1 or IgG4) provided by a heavy chain constant region gene.

The phrases "antibody that recognizes an antigen" and "antibody that is specific for an antigen" are used interchangeably herein with the term "antibody that specifically binds an antigen".

As used herein, an antibody or protein that "specifically binds to a pro-BDNF polypeptide" refers to an antibody or protein that binds to a human pro-BDNF polypeptide with a $K_D$ of 100 nM or lower, 10 nM or lower, 5 nM or lower. An antibody that "cross-reacts with an antigen other than pro-BDNF" refers to an antibody that binds the antigen with a $K_D$ of 10 nM or less, 5 nM or less. An antibody that "does not cross-react with a specific antigen" refers to an antibody that binds the antigen with a $K_D$ of 200 nM or more or a $K_D$ of 1 µM or more or a $K_D$ of 10 µM or more. In certain embodiments, such antibodies that do not cross-react with an antigen exhibit substantially undetectable binding to such proteins in standard binding assays.

As used herein, the term "$K_D$" refers to a dissociation constant obtained from a ratio of Kd to Ka (i.e., Kd/Ka) and expressed as a molar concentration (M). The $K_D$ value of an antibody can be determined using well-established methods in the art. The method for determining the KD of an antibody is well known to a skilled person in the art, for example, surface plasmon resonance operated as described in Examples, or a biosensor system such as the Biacore™ system.

As used herein, the term "affinity" or "affinity activity" refers to the strength of the interaction between an antibody and an antigen at a single antigenic site. As used herein, the term "high affinity" for an IgG antibody or a fragment thereof (e.g., a Fab fragment) refers to an antibody having a KD of $10^{-8}$M or lower, $10^{-9}$ M or lower for the target antigen. However, high-affinity binding can vary for other antibody isotypes.

As used herein, the term "selectivity" for an antibody or protein of the present disclosure refers to an antibody or protein that binds certain target polypeptides but does not bind closely related polypeptides. The phrases "antibody that recognizes an antigen" and "antibody that is specific for an antigen" are used interchangeably herein with the term "antibody that specifically binds an antigen".

The term "nucleic acid" or "polynucleotide" refers to deoxyribonucleic acid (DNA) or ribonucleic acid (RNA) and its polymers in single- or double-stranded form. Unless explicitly limited, the term includes nucleic acids containing analogs of known natural nucleotides that have similar binding properties as the reference nucleic acid and are metabolized in a manner similar to naturally occurring nucleotides. Unless otherwise indicated, a particular nucleic acid sequence also implicitly includes its conservatively modified variants (e.g., degenerate codon substitutions), alleles, orthologs, SNPs and complementary sequences, and explicitly indicated sequences. Specifically, degenerate codon substitution can be achieved by generating a sequence in which the third position of one or more selected (or all) codons is replaced by a mixed base and/or deoxyinosine residue (Batzer et al., Nucleic Acid).

As used herein, the term "treatment of a disease" (such as rheumatoid arthritis) refers, in one embodiment, to amelioration of a disease or disorder (i.e., slowing or preventing or reducing the progression of a disease or at least one of its clinical symptoms). In another embodiment, "treatment" refers to alleviation or improvement of at least one physical parameter, including physical parameters that may not be discernable by a patient. In another embodiment, "treatment" refers to modulation of a disease or disorder physically (e.g., stabilization of discernible symptoms), physiologically (e.g., stabilization of a physical parameter), or both. Unless explicitly described herein, methods for assessing the treatment and/or prevention of a disease are generally known in the art.

The percent identity between two nucleotide sequences can also be calculated using, for example, algorithms such as BLASTN program for nucleic acid sequences, using a word length (W) of 11, an expected value (E) of 10, M=5, N=4 and the comparison of two chains. The terms "cross-blocking" and "cross-preventing" are used interchangeably herein to refer to the interference of antibodies or other binding agents in the ability of other antibodies or binding agents to bind pro-BDNF in a standard competitive binding assay.

A standard competitive binding assay can be used to determine the ability or extent of an antibody or other binding agent, such as a protein comprising an antigen-binding portion of an antibody to interfere with binding of another antibody or binding molecule to pro-BDNF, and thus whether it can be considered as "cross-blocking" in accordance with the present disclosure. One suitable assay includes using Biacore™ technology (for example, by using a Biacore™ 3000 instrument (Biacore™, Uppsala, Sweden)), which can use surface plasmon resonance technology to measure the degree of interaction.

The term "variant" refers to other nucleic acids encoding antibodies of the present disclosure, including a nucleic acid mutated through nucleotide deletions, insertions or substitutions, while having at least 60, 70, 80, 90, 91, 92, 93, 94, 95, 96, 97, 98, 99, or 100% identity to the encoding nucleic acid sequence corresponding to CDRs, VLs, VHs, or light chains, or heavy chains, or scFv of the present disclosure or the like.

In some embodiments, a variant nucleic acid is included, in which the number of nucleotides that have been changed by nucleotide deletions, insertions, or substitutions in the CDR encoding region is no more than 1, 2, 3, 4, or 5, compared with the CDR encoding regions depicted herein.

For antibodies that bind the same epitope, VH, VL, full-length light and full-length heavy chain sequences (nucleotide and amino acid sequences) can be "mixed and matched" to generate other anti-pro-BDNF binding molecule of the present disclosure. The binding of such "mixed and matched" antibodies to pro-BDNF can be tested using the binding assays described above and other conventional binding assays (e.g., ELISA). When these strands are mixed and matched, VH sequences from a particular VH/VL pair should be replaced with structurally similar VH sequences. Likewise, the full-length heavy chain sequence from a particular full-length heavy/full-length light chain pair should be replaced with a structurally similar full-length heavy chain sequence. Likewise, VL sequences from a particular VH/VL pair should be replaced with structurally similar VL sequences. Likewise, full-length light chain sequences from a particular full-length heavy chain/full-length light chain pair should be replaced with structurally similar full-length light chain sequences.

Since each of these antibodies can bind pro-BDNF and the antigen-binding specificity is primarily rendered by CDR1, 2 and 3 regions, VH CDR1, 2 and 3 sequences can be "mixed and matched" with VL CDR1, 2 and 3 sequences (That is: CDRs from different antibodies can be mixed and matched, and each antibody containing VH CDR1, 2 and 3 and VL CDR1, 2 and 3 constitutes other anti-pro-BDNF binding molecules of the present disclosure). The binding of such "mixed and matched" antibodies to pro-BDNF can be tested using the binding assays described above and other conventional binding assays (e.g., ELISA). When VH CDR sequences are mixed and matched, the CDR1, CDR2 and/or CDR3 sequences from a particular VH sequence should be replaced with structurally similar CDR sequences. Likewise, when VL CDR sequences are mixed and matched, the CDR1, CDR2 and/or CDR3 sequences from a particular VL sequence should be replaced with structurally similar CDR sequences. It will be apparent to a skilled person in the art that novel VH and VH can be generated by replacing one or more VH and/or VL CDR region sequences with structurally similar sequences from the CDR sequences of the monoclonal antibodies of the disclosure shown herein.

As used herein, if the variable region chain or full-length chain of an antibody is obtained from a system using a human germline immunoglobulin gene, the human antibody contains heavy chain or light chain variable region or full-length heavy or light chain as a "product of" or "derived from" a particular germline sequence. Such systems include transgenic mice with a human immunoglobulin gene immunized with a target antigen, or a human immunoglobulin gene library screened with a target antigen and displayed on a phage. Human antibodies (as "products of" or "derived from" human germline immunoglobulin sequences) can be identified by comparing the amino acid sequence of a human antibody to the amino acid sequence of a human germline immunoglobulin and selecting the human germline immunoglobulin sequence that is closest in sequence to the sequence of the human antibody (i.e., maximum percent identity). Human antibodies as "products of" or "derived from" a particular human germline immunoglobulin sequence may contain amino acids different from the germline sequence due to, for example, naturally occurring somatic mutations or deliberate introduction from site-directed mutations. However, the selected human antibodies generally have at least 90% identity in the amino acid sequence to the amino acid sequence encoded by the human germline immunoglobulin gene, and contain amino acid residues, by which, when compared with amino acid sequences of germline immunoglobulins of other species (e.g. murine germline sequences), human antibodies can be identified as being of human. In some cases, a human antibody can have at least 60%, 70%, 80%, 90%, or at least 95% or even at least 96%, 97%, 98%, or 99% identity in amino acid sequence with the amino acid sequence encoded by a germline immunoglobulin gene. Generally, a human antibody derived from a particular human germline sequence will show a difference of no more than 10 amino acids, compared with the amino acid sequence encoded by the human germline immunoglobulin gene. In some cases, human antibodies may show a difference of no more than 5 or even no more than 4, 3, 2 or 1 amino acid, compared with the amino acid sequence encoded by the germline immunoglobulin gene.

Antibodies with Conservative Modification

In certain embodiments, an antibody (or an antigen-binding fragment thereof) of the present disclosure has a heavy chain variable region comprising HCDR1, HCDR2, and HCDR3 sequences (or HCDR1', HCDR2', and HCDR3') and light chain variable region comprising LCDR1, LCDR2 And LCDR3 sequences (or LCDR1', LCDR2' and LCDR3'), wherein one or more of these CDR sequences have a designated amino acid sequence or a conservative modification thereof based on the antibodies 1D3 or 2H8 described herein, and the antibody or protein retains the desired functional properties of the anti-pro-BDNF antibodies of the present disclosure.

As used herein, the term "conservative sequence modification" refers to an amino acid substitution in which an amino acid residue is replaced with an amino acid residue having a similar side chain. A family of amino acid residues with similar side chains has been defined in the art. These families include amino acids with basic side chains (e.g., lysine, arginine, histidine), amino acids with acidic side chains (e.g., aspartic acid, glutamic acid), amino acids with uncharged polar side chains (e.g., glycine, asparagine, glutamine, serine, threonine, tyrosine, cysteine, tryptophan), amino acids with non-polar side chains (e.g., alanine, valine, leucine, isoleucine, proline, phenylalanine, methionine), amino acids with β-branched side chains (e.g., threonine, valine Acids, isoleucines) and amino acids with aromatic side chains (e.g., tyrosine, phenylalanine, tryptophan, histidine). Therefore, one or more amino acid residues in the CDR region of an antibody of the present disclosure can be replaced with other amino acid residues from the same side chain family, and the functional assays described herein can be used to test the retaited function of altered antibodies.

Modifications can be introduced into the antibodies disclosed herein by standard techniques known in the art, such as site-directed mutagenesis and PCR-mediated mutagenesis.

Moreover, in addition to the recombinant antibodies 1D3 and 2H8 of the present invention, the present invention also includes homologous antibodies or proteins that retain the desired functional properties of 1D3 and 2H8 antibodies.

In particular, the homologous antibody or protein according to the present invention is an antibody or protein comprising an antigen-binding portion of an antibody against pro-BDNF polypeptide, which is characterized in that the antibody or protein:

i) binds the pro-BDNF polypeptide with a $K_D$ of 10 nM or less, as measured in, for example, the Biacore™ assay described in the Examples;

(ii) competitively inhibits binding of pro-BDNF to p75;

(iii) depends on the activity of pro-BDNF.

As used herein, "pro-BDNF-dependent activity" means that the antibody or protein of the invention has pro-BDNF-related activity. For example, if proBDNF binds to its ligand to promote a biological process, the antibody or protein of the present invention is an inhibitor or antagonist of the biological process; and if proBDNF binds to its ligand to inhibit a biological process, the antibody or protein of the present invention is an accelerator or agonist of the biological process.

Nucleic Acid Molecule Encoding an Antibody of the Invention

Another aspect of the invention relates to a nucleic acid molecule encoding an antibody or protein of the invention.

The invention also relates to nucleic acid molecules derived from the latter sequences, which have been optimized for protein expression in mammalian cells, such as CHO cell lines. The nucleic acid may be present in whole cells, in a cell lysate or may be a nucleic acid in a partially purified or substantially pure form. When purified by using standard techniques (including alkaline/SDS processing, CsCl banding, column chromatography, agarose gel electrophoresis, and other techniques known in the art) from other cellular components or other contaminants (such as other cellular nucleic acids or proteins), the nucleic acid is "isolated" or "becomes substantially pure". See, F. Ausubel et al., 1987, Current Protocols in Molecular Biology, Greene Publishing and Wiley Interscience, New York.

Nucleic acids of the invention can be obtained using standard molecular biology techniques. Once DNA fragments encoding, for example, VH and VL segments, are obtained, these DNA fragments can be further manipulated by standard recombinant DNA techniques, for example to convert a variable region gene into a full-length antibody chain gene, Fab fragment gene, or scFv gene. In these manipulations, a VL- or VH-encoding DNA fragment is effectively linked to another DNA molecule or a fragment encoding another protein, such as an antibody constant region or a flexible linker. The term "effectively linked", as used in this description, refers to the functional joining of two DNA fragments, for example, so that the amino acid sequence encoded by the two DNA fragments is retained in the frame or so that a protein can be expressed under the control of a desired promoter.

The isolated DNA encoding the VH region can be converted into a full-length heavy chain gene by efficiently linking the VH-encoding DNA to another DNA molecule encoding the heavy chain constant region (CH1, CH2, and CH3). The sequence of the human heavy chain constant region gene is known in the art (see, for example, Kabat, E A et al., 1991, Sequences of Proteins of Immunological Interest, 5th Edition, US Department of Health and Human Services, NIH Publication No. 91-3242). DNA fragments encoding these regions can be obtained by standard PCR amplification. The heavy chain constant region may be an IgG1, IgG2, IgG3, IgG4, IgA, IgE, IgM, or IgD constant region. In some embodiments, the heavy chain constant region is selected in IgG1 isotype. For the heavy chain gene of Fab fragment, the VH-encoding DNA can be efficiently linked to another DNA molecule merely encoding the CH1 constant region of the heavy chain.

The isolated DNA encoding the VL region can be converted into a full-length light chain gene (as well as Fab light chain gene) by efficiently linking the VL-encoding DNA to another DNA molecule encoding the light chain constant region CL. The sequence of the human light chain constant region gene is known in the art (see, for example, Kabat, E A et al., 1991, Sequences of Proteins of Immunological Interest, 5th Edition, US Department of Health and Human Services, NIH Publication No. 91-3242). DNA fragments containing these regions can be obtained by standard PCR amplification. The light chain constant region may be a κ or λ constant region.

To generate the scFv gene, the VH- and VL-encoding DNA fragments are efficiently linked to another fragment encoding a flexible linker, such as encoding amino acid sequence (Gly4-Ser)3, so that the VH and VL sequences can be expressed as a continuous single-chain protein, and the VL and VH regions are linked by the flexible linker (see, e.g., Bird et al., 1988, Science 242: 423-426; Huston et al., 1988, Proc. Natl. Acad. Sci. USA 85: 5879-5883; McCafferty et al., 1990, Nature 348: 552-554).

Isolation of the Recombinant Antibody of the Invention

A variety of methods for screening antibodies and proteins containing antigen-binding portions thereof have been described in the art. Such methods can be divided into in vivo systems, such as transgenic mice capable of producing full-length human antibodies upon antigen immunization, and in vitro systems that generate a library of antibody-encoding DNA. These in vitro technologies are called display technologies and include, but are not limited to, phage display, RNA or DNA display, ribosome display, yeast or mammalian cell display. They have been extensively described in the art (for a review see, for example, Nelson et al., 2010, Nature Reviews Drug discovery, "Development trends for human monoclonal antibody therapeutics"). In a specific embodiment, human recombinant antibodies of the present disclosure are isolated using libraries for screening human recombinant antibodies and phage display methods.

The library of VH and VL genes or related CDR regions can be individually cloned by polymerase chain reaction (PCR) or synthesized by a DNA synthesizer, and randomly recombined in a phage library, and then antigen-binding clones can be selected.

Such phage display methods for isolating human antibodies have been established in the art or are described in the examples below. See, for example: U.S. Pat. Nos. 5,223,409; 5,403,484; 5,427,908; 5,580,717; 6,521,404, and the like.

Preparation of Monoclonal Antibody-Producing Transfected Tumors

Antibodies of the present disclosure can be produced in host cell transfected tumors using, for example, a combination of recombinant DNA technology and gene transfection methods known in the art (e.g., Morrison, S. 1985, Science 229: 1202).

For example, in order to express antibodies or antibody fragments thereof, DNA encoding partial or full-length light and heavy chains can be obtained using standard molecular biology or biochemical techniques (e.g., DNA chemical synthesis, PCR amplification, or using hybridomas expressing the antibody of interest) CDNA clones), and the DNA can be inserted into an expression vector so that the genes are efficiently linked to transcription and translation control sequences. In the present specification, the term "efficiently linked" is intended to mean that an antibody gene is linked into a vector such that the transcription and translation control sequences within the vector perform their predetermined function of regulating the transcription and translation of the antibody gene. An expression vector and expression control sequence that are compatible with the used expression host cell are selected. The antibody light chain gene and the antibody heavy chain gene can be inserted into different vectors, or more commonly, both genes are inserted into a same expression vector. The antibody gene is inserted into an expression vector by standard methods (e.g., linking the antibody gene fragment to a complementary restriction site on the vector, or blunt-ended ligation if no restriction site is present). The light and heavy chain variable regions of the antibodies described herein can be used to generate full-length antibody genes of any antibody isotype by inserting them into an expression vector encoding a heavy chain constant region and a light chain constant region of a desired isotype, thereby effectively linking the VH segment to the CH segment in the vector, and effectively linking the VL segment to the CL segment in the vector.

To express light and heavy chains, standard techniques are used to transfect expression vectors encoding heavy and light chains into host cells. The term "transfection" in various forms is intended to encompass a variety of techniques commonly used to introduce foreign DNA into a prokaryotic or eukaryotic host cell, such as electroporation, calcium phosphate precipitation, DEAE-dextran transfection, and the like. It is theoretically possible to express antibodies of the present disclosure in either prokaryotic or eukaryotic host cells. Preferably, the antibodies are expressed in eukaryotic cells such as mammalian host cells, yeast or filamentous fungi, since compared with prokaryotic cells, such eukaryotic cells (especially mammalian cells) are more likely to assemble and secrete correctly folded and immunologically active antibodies.

Bispecific Molecule

In another aspect, the invention characterized a bispecific or multispecific molecule comprising an anti-proBDNF antibody of the present disclosure or a protein comprising an antigen-binding portion thereof. An antibody or protein of the invention can be derivatized or linked to another functional molecule, such as another peptide or protein (e.g., another antibody or ligand for a receptor) to produce a bispecific molecule binding to at least two different binding sites or target molecules. The antibodies or proteins of the invention can, in fact, be derivatized or linked to more than one other functional molecule to produce multispecific molecules that bind to more than two different binding sites and/or target molecules; and such multispecific molecules are also intended to be encompassed by the term "bispecific molecule" as used herein. To generate a bispecific molecule of the invention, an antibody or protein of the invention can be functionally linked (e.g., by chemical coupling, gene fusion, non-covalent association or other means) to one or more other binding molecules, such as another antibody, antibody fragment, peptide or binding mimetic in order to generate a bispecific molecule.

Accordingly, the invention includes a bispecific molecule comprising at least one binding specific portion against pro-BDNF or a fragment thereof (e.g., SEQ ID NO: 41, 44, or 47). For example, the second target epitope is another epitope of pro-BDNF that is different from the first target epitope. Another example is a bispecific molecule comprising at least one first binding specific portion (e.g., an antigen-binding portion of 1D3 or 2H8) against pro-BDNF and a second binding specific portion against an epitope elsewhere in pro-BDNF or within another target antigen.

Multivalent Antibody

In another aspect, the invention provides a multivalent antibody comprising at least two identical or different antigen-binding portions of an antibody of the invention that binds pro-BDNF (e.g., an antigen-binding portion selected from 1D3 or 2H8). In one embodiment, the multivalent antibody provides antigen-binding portions of at least 2, 3, or 4 antibodies. The antigen-binding portions can be linked together by protein fusion or covalent or non-covalent linkage. Alternatively, ligation methods have been described for bispecific molecules. A tetravalent compound can be obtained, for example, by cross-linking an antibody of the invention with an antibody that binds to a constant region, such as an Fc or hinge region, of an antibody of the invention.

Pharmaceutical Composition

In another aspect, the invention provides a composition, such as a pharmaceutical composition, comprising one or a set of antibodies of the present disclosure or a protein comprising an antigen-binding portion thereof (an antibody selected from 1D3 or 2H8) formulated with a pharmaceutically acceptable carrier. Such composition may comprise one or a set (e.g., two or more different) antibodies of the invention. For example, a pharmaceutical composition of the invention may comprise a set of antibodies or proteins that bind different epitopes on a target antigen or have complementary activities.

The pharmaceutical composition of the present invention can also be administered in combination therapy (i.e., in combination with other drugs). For example, the combination therapy may include an anti-pro-BDNF antibody or protein of the invention (e.g., an antibody selected from 1D3 or 2H8) in combination with at least one other anti-inflammatory agent or another chemotherapeutic agent (e.g., an immunosuppressant).

As used herein, a "pharmaceutically acceptable carrier" includes any and all physiologically compatible solvents, dispersion media, coatings, antibacterial and antifungal agents, isotonic and absorption delaying agents, and the like. The carrier should be suitable for intravenous, intramuscular, subcutaneous, parenteral, spinal or epidermal administration (e.g., by injection or infusion). In one embodiment, the carrier should be suitable for the subcutaneous route. The active compound, i.e. an antibody, immunoconjugate or bispecific molecule, may be, depending on the route of administration, coated in a substance to protect the compound from acids and other natural conditions that can inactivate the compound.

The pharmaceutical composition of the present invention may contain one or more pharmaceutically acceptable salts. "Pharmaceutically acceptable salt" refers to a salt that retains the desired biological activity of the parent compound without producing any adverse toxicological effects (see, for example, Berge, S M et al., 1977, J. Pharm. Sci. 66: 1-19). Examples of such salts include acid addition salts and base addition salts.

Acid addition salts include salts derived from non-toxic inorganic acids, such as hydrochloric acid, nitric acid, phosphoric acid, sulfuric acid, hydrobromic acid, hydroiodic acid, phosphorous acid, and the like, and derived from non-toxic organic acids, such as aliphatic monocarboxylic acids and Salts of dicarboxylic acids, phenyl-substituted alkanoic acids, hydroxyalkanoic acids, aromatic acids, aliphatic and aromatic sulfonic acids, and the like. Base addition salts include salts derived from alkaline earth metals (such as sodium, potassium, magnesium, calcium, etc.) and salts derived from non-toxic organic amines, such as N, N'-dibenzylethylenediamine, N-methylglucamine, chloroprocaine, choline, diethanolamine, ethylenediamine, procaine, etc.

The pharmaceutical composition of the present invention may further include a pharmaceutically acceptable antioxidant. Examples of pharmaceutically acceptable antioxidants include: water-soluble antioxidants, such as ascorbic acid, cysteine hydrochloride, sodium bisulfate, sodium metabisulfite, sodium sulfite, etc.; oil-soluble antioxidants, such as ascorbyl palmitate, butylated hydroxyanisole Ether (BHA), butylated hydroxytoluene (BHT), lecithin, propyl gallate, α-tocopherol, etc.; and metal chelating agents, such as citric acid, ethylenediaminetetraacetic acid (EDTA), sorbitol, tartaric acid, phosphoric acid, etc.

Examples of suitable aqueous and non-aqueous carriers that can be used in the pharmaceutical composition of the present invention include water, ethanol, polyol (such as glycerol, propylene glycol, polyethylene glycol, etc.) and suitable mixtures thereof, vegetable oils such as olive oil, and injectable organic esters, such as ethyl oleate. Proper fluidity can be maintained, for example, by using a coating material, such as lecithin, maintaining the desired particle size in the case of dispersion, and using a surfactant.

These compositions may also contain adjuvants, such as preservatives, wetting agents, emulsifying agents and dispersing agents. Prevention of the presence of microorganisms can be ensured by sterilization methods and including various antibacterial and antifungal agents such as parabens, chlorobutanol, phenol, sorbic acid, and the like. It may also be desirable to add isotonic agents, such as sugars, sodium chloride, and the like to the composition. In addition, a prolonged absorption of injectable drugs can be achieved by the addition of absorption-delaying substances, such as aluminum monostearate and gelatin.

Pharmaceutically acceptable carriers include sterile aqueous solutions or dispersions and sterile powders for the immediate preparation of sterile injectable solutions or dispersions. Using such media and agents for pharmaceutically active substances is known in the art. Except insofar as any conventional media or drug is incompatible with the active compound, its use in the pharmaceutical composition of the present invention is envisaged. Supplementary active compounds can also be incorporated into the composition.

Therapeutic compositions must generally be sterile and stable under the conditions of manufacture and storage. The composition can be formulated as a solution, microemulsion, liposome, or other ordered structure suitable for high drug concentration. The carrier can be a solvent or dispersion medium containing, for example, water, ethanol, polyol (for example, glycerol, propylene glycol, and liquid polyethylene glycol, and the like), and suitable mixtures thereof. Proper fluidity can be maintained, for example, by using a coating such as lecithin, maintaining the desired particle size in the case of dispersions, and using surfactants. In many cases, isotonic agents, for example, sugars, polyalcohols such as mannitol, sorbitol, or sodium chloride may be included in the composition. Prolonged absorption of injectable compositions can be achieved by including absorption-delaying agents in the composition, such as monostearate and gelatin.

A review of the development of stable protein (e.g., antibody) formulations can be found in Cleland et al., 1993, Crit. Reviews. Ther. Drug Carrier Systems 10 (4): 307-377 and Wei Wang 1999, Int. J. Pharmaceutcs 185: 129-88. Additional discussions on formulation of antibodies can be found, for example, in Daugherty and Mrsny 2006, Advanced Drug Delivery Reviews 58: 686-706; U.S. Pat. No. 6,171,586 and other known references.

Solutions or suspensions for intradermal or subcutaneous administration typically contain one or more of the following components: sterile diluents, such as water for injection, saline solution, non-volatile oil, polyethylene glycol, glycerol, propylene glycol, or other synthetic solvents; antibacterial agents, such as benzyl alcohol or methyl paraben; antioxidants, such as ascorbic acid or sodium bisulfite; chelating agents, such as ethylenediaminetetraacetic acid; buffering agents, such as acetate, citrate or phosphate; and tonic agents, such as sodium chloride or glucose. pH can be adjusted with acids or bases, such as hydrochloric acid or sodium hydroxide. Such formulations can be enclosed in ampoules, disposable syringes or multiple dose vials made of glass or plastic.

Sterile injection solutions can be prepared by incorporating the required amount of the active compound with one or a group of the ingredients listed above as necessary into a suitable solvent, followed by microfiltration and sterilization. Generally, dispersions are prepared by incorporating the antibodies or proteins of the present disclosure into a sterile vehicle that contains a basic dispersion medium and the required other ingredients from those enumerated above. In the case of sterile powders for preparing a sterile injectable solution, the preparation method is vacuum drying and freeze drying (lyophilization), and the method produces powders containing the active ingredient from previously filtered sterilized solution and any additional desired ingredients.

The amount of active ingredient that can be combined with a carrier material to produce a single dosage form will vary depending on the subject to be treated and the particular mode of administration. The amount of active ingredient that can be combined with a carrier material to produce a single dosage form is generally the amount of the composition that produces therapeutic effects.

A "therapeutically effective amount" of an anti-pro-BDNF antibody or protein of the present disclosure can lead to a reduction in the severity of disease symptoms, an increase in the frequency and duration of disease-free periods, or the prevention of damage or disability caused by the disease.

Compositions of the present disclosure can be administered using one or more methods known in the art via one or more routes of administration. As will be understood by a skilled person in the art, the route and/or mode of administration will vary depending on the desired result. The routes of administration of antibodies of the present disclosure include intravenous, intramuscular, intradermal, intraperitoneal, subcutaneous, spinal, or other parenteral routes of administration, such as injection or infusion. As used herein, the phrase "parenteral administration" means a mode of administration other than enteral and topical administration, usually by injection, including but not limited to intravenous, intramuscular, intraarterial, intrathecal, intrasaccular, intraorbital, Intracardiac, intradermal, intraperitoneal, transtracheal, subcutaneous, subepidermal, intraarticular, subcapsular, subarachnoid, intraspinal, epidural and intrastemal injections and infusions.

Alternatively, the antibodies or proteins of the disclosure can be administered by a non-parenteral route, such as a topical, epidermal, or mucosal route of administration, for example, intranasal, oral, vaginal, rectal, sublingual, or topical administration.

The antibodies or proteins of the present disclosure can be prepared with carriers that will protect the antibodies from rapid release, such as controlled release formulations, including implants, transdermal patches, and microencapsulated delivery systems. Biodegradable, biocompatible polymers can be used, such as ethylene vinyl acetate, polyanhydrides, polyglycolic acid, collagen, poly-n-esters, and polylactic acid. Many methods for preparing such dosage forms have been patented or known to a skilled person in the art. See, for example, Sustained and Controlled Release Drug Delivery Systems, edited by J. R. Robinson, Marcel Dekker, Inc., New York, 1978.

Therapeutic compositions can be administered using medical means known in the art. For example, in one embodiment, the therapeutic compositions of the present disclosure may be administered by needleless subcutaneous injection means, such as the means disclosed in U.S. Pat. Nos. 5,399,163; 5,383,851; 5,312,335; and the like.

Examples of well-known implants and modules that can be used in the present disclosure include: U.S. Pat. No. 4,487,603, which disclosed an implantable microinfusion pump for dispensing a drug at a controlled rate; U.S. Pat. No. 4,486,194, which disclosed a therapeutic device for administering a drug via skin; U.S. Pat. No. 4,447,233, which disclosed a drug infusion pump for delivering drugs at a precise infusion rate; U.S. Pat. No. 4,447,224, which showed a variable flow implantable infusion devices for continuous drug delivery; U.S. Pat. No. 4,439,196, which disclosed an osmotic drug delivery system with a multi-compartment compartment; and U.S. Pat. No. 4,475,196, which disclosed an osmotic drug delivery system. Many other such implants, delivery systems, and modules are known to a skilled person in the art.

In certain embodiments, antibodies or proteins of the disclosure can be formulated to ensure proper distribution in the body. For example, the blood-brain barrier (BBB) excludes many highly hydrophilic compounds. To ensure that the therapeutic compounds of the present disclosure cross the BBB (if needed), they can be formulated in, for example, liposomes. Methods of making liposomes can be found, for example, in U.S. Pat. Nos. 4,522,811, 5,374,548, and 5,399,331. The liposomes may comprise one or more moieties that are selectively transported to specific cells or organs to enhance targeted drug delivery (see, for example, V. V. Ranade 1989, J. Cline Pharmacol. 29: 685). Exemplary targeting moieties include folic acid or biotin (see, for example, U.S. Pat. No. 5,416,016 to Low et al.), Mannoside (Umezawa et al., 1988, Biochem. Biophys. Res. Commun. 153: 1038); antibodies (PGBloeman et al., 1995, FEBS Lett. 357: 140; M. Owais et al., 1995, Antimicrob. Agents Chernother. 39: 180); Surfactant A protein receptor (Briscoe et al., 1995, Am. J. Physiol. 1233: 134); p 120 (Schreier et al., 1994, J. Biol. Chem. 269: 9090); see also Keinanen and Laukkanen, 1994, FEBS Lett. 346: 123; Killion and Fidler, 1994, Immuno methods 4: 273.

Uses and Methods of the Invention

The antibodies or proteins of the invention have diagnostic and therapeutic functions in vitro and in vivo. For example, these molecules can be administered to cells in culture (e.g., in vitro or in vivo) or in a subject (e.g., in vivo) to treat, prevent or diagnose a variety of conditions.

The method is particularly suitable for the treatment, prevention or diagnosis of pro-BDNF-related disorders and/or autoimmune and inflammatory disorders, such as multiple sclerosis, rheumatoid arthritis or psoriasis; or for analgesia.

Specifically, the invention provides methods for treating pro-BDNF-related disorders and/or autoimmune and inflammatory disorders, or analgesia. In certain embodiments, the method includes the step of administering to the subject in need thereof an isolated antibody of the invention or a protein comprising an antigen-binding portion thereof.

The present invention also provides a method for attenuating or inhibiting the signal transduction response induced by pro-BDNF or pro-BDNF in target cells or tissues by contacting the cells with a composition comprising a therapeutically effective dose of an antibody of the disclosure.

In this specification, the phrase "pro-BDNF-mediated disease" or "pro-BDNF-related disorder" includes all diseases and medical conditions in which pro-BDNF or pro-BDNF play a role (whether directly or indirectly) in a disease or medical condition, including the cause, development, progression, persistence or pathology of the disease or condition. Therefore, these terms include a condition that is associated with or characterized by abnormal pro-BDNF levels and/or a disease or condition that can be treated by attenuating or inhibiting activities induced by pro-BDNF in target cells or tissues (e.g., TNF-$\alpha$, IL-2, IL-6 or IL-4 production). Such diseases or conditions include inflammatory conditions and autoimmune diseases, such as multiple sclerosis, asthma, arthritis, rheumatoid arthritis or psoriasis. Such diseases also include allergies and allergic conditions, hypersensitivity, chronic obstructive pulmonary disease, cystic fibrosis, and rejection of organ or tissue transplants.

The antibodies or proteins of the invention can be used (but not limited to) to treat, prevent, or ameliorate autoimmune diseases or inflammatory conditions, especially inflammatory conditions, etiology of which involves autoimmune components, such as arthritis (e.g. rheumatoid arthritis, arthritis chronica progrediente and deformity arthritis) and rheumatic diseases, including inflammatory conditions and rheumatic diseases involving bone loss, inflammatory pain, arthropathy (including ankylosing spondylitis), Wright's syndrome, reactive arthritis, psoriatic arthritis, juvenile idiopathic arthritis and bowel disease arthritis, start and stop inflammation, hypersensitivity (including airway hypersensitivity and skin hypersensitivity) and allergies. Specific autoimmune diseases for which the antibodies of the present disclosure can be used include autoimmune hematological disorders (including, for example, hemolytic anemia, aplastic anemia, pure red blood cell anemia, and idiopathic thrombocytopenia), systemic lupus erythematosus ((SLE), lupus nephritis, inflammatory muscle disease (dermatomyositis), periodontitis, polychondritis, scleroderma, Wegener's granulomatosis, dermatomyositis, chronic active hepatitis, myasthenia gravis, psoriasis, Stephen Johnson syndrome, spontaneous oral inflammatory diarrhea, autoimmune inflammatory bowel disease (including, for example, ulcerative colitis, Crohn's disease and irritable bowel syndrome), endocrine eye disease, Graves' disease, Sarcoidosis, Multiple Sclerosis, Systemic Sclerosis, Fibrosis, Primary Biliary Cirrhosis, Juvenile Diabetes (Type 1 Diabetes), Uveitis, Dry Keratoconjunctivitis and Spring Keratoconjunctivitis, Pulmonary fibrosis, periprosthetic osteolysis, glomerulonephritis (with and without nephrotic syndrome, including, for example, idiopathic nephrotic syndrome or micropathic nephropathy), multiple myeloma, other types Tumors, inflammatory diseases of the skin and cornea, myositis, loosening of bone implants, metabolic disorders (such as obesity, atherosclerosis and other cardiovascular diseases, including dilated cardiomyopathy, myocarditis, type II diabetes, and dyslipidemia) and autoimmune thyroid diseases (including Hashimoto's thyroiditis), small and medium vascular primary vasculitis, large vasculitis including giant cell arteritis, suppurative sweat glanditis, optic neuromyelitis, Sjogren's syndrome, Behcet's disease, atopic and contact dermatitis, bronchiolitis, inflammatory muscle disease, autoimmune peripheral neuropathy, immune kidney, liver and thyroid disease, inflammation and atherosclerosis, autoinflammatory fever syndrome, immune hematological disorders, and bullous diseases of the skin and mucous membranes. Anatomically, uveitis can be anterior, middle, posterior, or panuveitis. It can be chronic or acute. The etiology of uveitis can be autoimmune or non-infectious, infectious, associated with systemic disease or white spot syndrome.

The antibodies or proteins of the present disclosure can also be used to treat, prevent or ameliorate asthma, bronchitis, bronchiolitis, idiopathic interstitial pneumonia, pneumoconiosis, emphysema, and other obstructive or inflammatory diseases of the airways.

The antibodies or proteins of the present disclosure are also useful in diseases of bone metabolism, including osteoarthritis, osteoporosis, and other inflammatory arthritis and general bone loss, including age-related bone loss, especially periodontal disease.

The following diseases include particularly preferred targets for treatment with antibodies of the invention or proteins comprising antigen-binding portions thereof: multiple sclerosis, psoriasis, asthma, systemic lupus erythematosus (SLE), and lupus nephritis.

The antibody or protein of the invention can be used as the sole active ingredient or in combination with other drugs such as immunosuppressants or immunomodulators or other anti-inflammatory agents or other cytotoxic or anti-cancer agents (e.g. as an adjuvant or a combination thereof), for example, to treat or prevent the aforementioned diseases. For example, the antibodies of the present invention can be used in combination with following medicaments: DMARD, such as gold salts, sulfasalazine, antimalarials, methotrexate, D-penicillamine, azathioprine, mycophenolic acid, tacrolimus, sirolimus, dimethylamine tetracycline, Leflunomide, glucocorticoids; calcineurin inhibitors, such as cyclosporin A or FK 506; modulators of lymphocyte recycling, such as FTY720 and FTY720 analogs; mTOR inhibitors, such as rapamycin, 40-O-(2-hydroxyethyl)-rapamycin, CCI779, ABT578, AP23573 or TAFA-93; ascomycin with immunosuppressive properties, such as ABT-281, ASM981, etc.; corticosteroids; Cyclophosphamide; Azathioprine; Leflunomide; Mizoribine; Morphine mycophenolate; 15-deoxyspergualin or immunosuppressive homologues, analogs or derivatives thereof; immunosuppressive monoclonal antibodies, such as monoclonal antibodies against leukocyte receptors, for example, MHC, CD2, CD3, CD4, CD7, CD8, CD25, CD28, CD40, CD45, CD58, CD80, CD86 or ligands thereof; other immunomodulatory compounds, such as recombinant binding molecules with at least a portion of the extracellular domain of CTLA4 or a mutant thereof, such as at least a portion of the extracellular domain of CTLA4 or a mutant thereof linked to a non-CTLA4 protein sequence, such as CTLA4Ig (e.g., designated as ATCC 68629) or mutants thereof, such as LEA29Y; adhesion molecule inhibitors, such as LFA-1 antagonists, ICAM-1 or -3 Antagonists, VCAM-4 antagonists or VLA-4 antagonists; or chemotherapeutics, such as paclitaxel, gemcitabine, cisplatin, doxorubicin or 5-fluorouracil; anti-TNF drugs, such as monoclonal antibodies against TNF, such as Infinee Cilimab, adalimumab, CDP870 or a receptor construct against TNF-RI or TNF-RII, such as etanercept, PEG-TNF-RI; a blocker of a pro-inflammatory cytokine, an IL1 blocker, for example anakinra or IL1 trap, Kananumab, IL13 blocker, IL4 blocker, IL6 blocker, IL17 blocker (such as secukinumab, broadalumab, ixekizumab); chemokine blocking agents, for example proteases (such as metalloproteinase) inhibitors or activators, anti-IL15 antibodies, anti-IL6 antibodies, anti-IL4 antibodies, anti-IL13 antibodies, anti-CD20 antibodies, NSAIDs, such as aspirin or anti-infective agents (not limited to the mentioned reagents).

The present invention will be further described below with reference to specific embodiments. It should be understood that these examples are only used to illustrate the present invention and not to limit the scope of the present invention. The experimental methods without specific conditions in the following examples are generally based on the conventional conditions such as J. Sambrook et al., Molecular Cloning Experiment Guide, Third Edition, Science Press, 2002, or according to the conditions recommended by the manufacturer.

Example 1

Expression and Purification of Human proBDNF Precursor Domain Protein (1) Construction and Identification of pET22b-proBDNF Vector cDNA of human tumor cell U87MG was used as a template (purchased from RAYGENE), and primers PROBDNF-F (SEQ ID No: 25) and PROBDNF-R (SEQ ID No: 26) were used for PCR amplification to obtain proBDNF gene fragment (703 bp) with restriction sites ECORI/XhoI at both ends, which was double-digested with ECORI/XhoI (purchased from NEB) to obtain the target gene fragment proBDNF. The vector plasmid pET22b (purchased from Novogen) was double-digested with ECORI/XhoI, and the vector fragment was recovered after agarose gel electrophoresis and ligated with the aforementioned target gene fragment proBDNF under the action of T4 ligase (purchased from NEB) and then transformed into Escherichia coli TOP 10 (purchased from LIFE). The cells were screened based on ampicillin resistance, and the positive clones containing the inserted fragment were identified by ECORI/XhoI digestion, and verified by sequencing to obtain the prokaryotic expression plasmid pET22b-proBDNF containing the correct human proBDNF gene sequence.

(2) Expression and Purification of Human proBDNF Protein

The pET22b-proBDNF plasmid was transformed into the expression host strain BL21 (DE3) (purchased from Novagen), plated on an ampicillin-resistant plate and inversion-incubated at 37° C. overnight. A single clone was selected for inducible expression, shaken and cultured to an OD600 of 0.6-0.8. IPTG was added to a final concentration of 1 mM, and induced at 30° C. for 4 hours. Afterwards, the bacterial solution was collected. The pellet was collected by centrifugation, resuspended in 1/10 volume of buffer A (50 mM $NaH_2PO_4$, 300 mM NaCl, 10 mM imidazole, pH 8.0). PMSF (final concentration: 1 mM) was added, sonicated on ice, and centrifuged (4° C., 12000 g) for 15 min, thereby collecting the supernatant. Purification by Ni-NTA Agarose (purchased from QIAGEN) affinity column chromatography was conducted to obtain the expressed protein of interest. Then the PBS solution was subjected to dialysis, and the purity of the purified protein upon dialysis was analyzed by 12% SDS-PAGE analysis. The amount of the protein was detected by A280 and its molecular weight was determined by SDS PAGE electrophoresis. The results showed that the molecular weight of the target band was around 30 kD, which was basically consistent with the theoretical molecular weight of proBDNF molecule of 27.8 kD.

(3) Construction of Human proBDNF Precursor Domain Expression Vector V5F-Pro-Domain The plasmid pET22b-proBDNF obtained above was used as a template, primers BDNFproVF1 (SEQ ID NO: 28) and BDNFproVR1 (SEQ ID NO: 29) were used for PCR amplification to obtain human proBDNF precursor domain gene fragment (350 bp) with restriction sites NheI/XhoI at both ends. This PCR fragment was double-digested with the restriction enzyme NheI/XhoI (purchased from NEB), and the obtained precursor domain gene fragment and vector V5F (Purchased from RAYGENE) which was double-digested with the same NheI/XhoI (purchased from NEB) were ligated by T4 DNA ligase, and transformed into host strain TOP10 (purchased from LIFE). Positive clones were picked for PCR identification, and verified by sequencing, thereby successfully constructing the V5F-pro-domain plasmid.

(4) Expression and Purification of Human proBDNF Precursor Domain Protein

Well-grown HEK293F cells (HEK293F, purchased from LIFE) were inoculated into a cell triangle culture flask at a density of $1\times10^6$ cells/ml, and cultured overnight at 37° C., 5% $CO_2$ and 120 rpm. The V5F-pro-domain plasmid obtained in the above step and liposomes (293 Fectin, purchased from LIFE) were diluted with DMEM respectively and mixed gently, incubated at room temperature for 20 min. The incubated DNA-liposome complex was added to HEK293F cells and incubated at 37° C., 5% $CO_2$ and 120 rpm for 72 h. The cell culture solution was collected, centrifuged at 4500 g for 15 min to discard the cells and obtain the supernatant. 1 ml of FLAG antibody affinity filler (ANTI-FLAG Agarose Affinity Gel, purchased from Sigma-Aldrich) was taken and loaded on a column. The FLAG affinity column was equilibrated with lysis buffer (50 mM PB, 0.3 M NaCl, 5% glycerol) for 5-10 column volumes. The supernatant of the centrifuged cell culture solution flowed through the FLAG affinity column at 1 ml/min and the flow-through fluid was stored at 4° C. The column was washed with 5-10 column volumes of washing buffer 1 (50 mM PB, pH 7.8, 0.3 M NaCl, 5% glycerol), and washing liquid 1 was collected and stored at 4° C. The column was washed with 4-5 column volumes of washing buffer 2 (50 mM PB, pH 7.8, 0.5 MNaCl, 5% glycerol), and washing liquid 2 was collected and stored at 4° C. The column was washed with 4-5 column volumes of elution buffer (50 mM Glycine. HCl, pH 3.0, 0.3 M NaCl, 5% glycerol), the eluate was collected, a neutralization buffer (1M Tris.HCl pH8.0) was added, and dialyzed against dialysis liquid (50 mM PB, pH7.8, 0.3M NaCl, 5% glycerol) at 4° C. overnight. SDS PAGE electrophoresis showed the molecular weight of target band is comparable to the theoretical molecular weight of human proBDNF precursor domain protein, 13 kD.

Example 2

Screening of Single-Chain Antibody of Human proBDNF Precursors 2.1 Screening of Binding Antibodies Specific for Human proBDNF Precursor Protein based on Phage Display Antibodies specific for human proBDNF precursor protein were screened from a fully human natural antibody library using phage display technology. To this end, phage display libraries were prepared using conventional phage display methods in the art, and four rounds of targeted screening were performed on biotin-labeled human proBDNF precursor recombinant proteins. The preparation methods and display methods of phage display libraries were performed by conventional operations in the art Perform as described in PCT/CN2016/096292, Antibody Phage Display (edited by Robert Aitken).

2.2 Identification of Binding Antibodies Specific for Human proBDNF Precursor

Ninety-six clones were randomly selected from the fourth round of screening, and single-phage ELISA (enzyme-linked immunosorbent assay) was used to analyze their binding ability to human proBDNF precursors. For this purpose, each single colony was inoculated into 300 µl of 2×YT/ampicillin medium (containing 2% glucose) in a 96-well deep-well culture plate, shaken and cultured at 37° C. and 250 rpm for 16 hours. 20 µl of the culture was inoculated into 500 µl of 2×YT/ampicillin medium (containing 0.1% glucose), and shaken and cultured at 37° C. and 250 rpm for 1.5 hours. For preparing helper phage solution, 75 µl of M13KO7 (titer: $3\times10^{12}$ pfu/ml) was taken and mixed into 15 ml of 2×YT medium, added to the culture plate at 50 µl/well, and incubate at 37° C. and 150 rpm for 30 minutes. And then, the prepared kanamycin solution was added at 50 µl/well (180 µl of 50 mg/ml kanamycin was taken and added to 15 ml 2×YT medium), and shaken and cultured at 37° C. and 250 rpm for 16 hours. Finally, the cells were pelleted by centrifugation (30 minutes, 5000×g, 4° C.), and the supernatant was transferred to a new 96-well deep-well culture plate.

To perform a single phage ELISA, a 96-well MediSorp ELISA plate (purchased from Nunc) was coated with 100 ng/well antigen human proBDNF precursor and negative control protein BSA (100 µl/well) respectively, overnight at 4° C. Each well was blocked with PBST containing 2% BSA (w/v). The wells were then washed for three times with PBST. Then 100 µl/well of each phage solution prepared above was added to each well on the plate. After incubated at 37° C. for 2 hours, the plate was washed for three times with PBST. To detect bound phage, an anti-M13 antibody peroxidase dismutase conjugate (purchased from GE Healthcare) was diluted in PBST at 1:5000 and 100 µl was added to each well. After incubated at 37° C. for 1 hour, the wells were rinsed for three times with PBST and then three times with PBS. Finally, 50 µl of TMB substrate was pipetted into the wells, and developed at room temperature for 10 minutes. Then, 50 µl of 2 M $H_2SO_4$ was added to each well to quench the color development reaction. The extinction value was measured at 450 nm using an enzyme-linked immunoassay device (Bio-Rad).

In combination with sequencing analysis, strong binding signals to human proBDNF precursor protein were observed for single-chain antibodies 1D3 (see SEQ ID NO: 22 for the nucleotide sequence and SEQ ID NO: 21 for the amino acid sequence) and 2H8 (see SEQ ID NO: 24 for the nucleotide sequence and 23 for the amino acid sequence) in ELISA experiment, but these antibodies did not bind to BSA (FIG. 1). The corresponding plasmids for two antibodies are pCantab-1D3 and pCantab-2H8.

Example 3

Preparation of Monoclonal Antibody for Human proBDNF Precursor Protein

In this example, a two-plasmid system was used for expressing the monoclonal antibody. It is necessary to construct the gene of the antibody heavy chain variable region into a pIH plasmid containing human IgG1 CH gene, and the gene of the antibody light chain variable region into PIK plasmid containing human IgG CL gene (plasmid was purchased from Shanghai Ruijin Biotechnology Co., Ltd.), respectively.

A primer pair 1D3-HF (SEQ ID NO: 30) and 1D3-HR (SEQ ID NO: 31) were used to amplify the VH-1D3 fragment from the template plasmid pCantab-1D3; a primer pair HF1F (SEQ ID NO: 32) and HF1R (SEQ ID NO: 33) were used to amplify the HF1 fragment from the template plasmid pIH; and a primer pair HF3F (SEQ ID NO: 34) and HF3R (SEQ ID NO: 35) was used to amplify the HF3 fragment from the template plasmid pIH. The three fragments were mixed at equimolar ratio and subjected to splicing PCR. Fragments were recovered, double-digested with restriction enzymes NheI/NotI, ligated with vector plasmid pIH which was also double-digested with NheI/NotI by using T4 DNA ligase, and transformed into the host strain TOP10. Clones were selected, and positive clones were identified by PCR and confirmed by sequencing to obtain a pIH-1D3 eukaryotic expression plasmid. A pIH-2H8 eukaryotic expression plasmid was also obtained in the same manner.

To obtain pIK-1D3 eukaryotic expression plasmid, a primer pair 1D3-LF (SEQ ID NO: 36) and 1D3-LR (SEQ ID NO: 37) were used to amplify the VL-2H8 fragment from the template plasmid pCantab-2H8; a primer pairs LF1F (SEQ ID NO: 38) and LF1R (SEQ ID NO: 39) were used to amplify the LF1 fragment from the template plasmid pIK. The two fragments were mixed in equimolar ratio and subjected to splicing PCR. Fragments were recovered, double-digested with restriction enzymes EcoRV/BsiWI, ligated with vector plasmid pIK which was also double-digested with EcoRV/BsiWI by using T4 DNA ligase, and transformed into the host strain TOP10. Clones were selected, and positive clones were identified by PCR and confirmed by sequencing. A pIK-2H8 eukaryotic expression plasmid was also obtained in the same manner.

Figure 2:
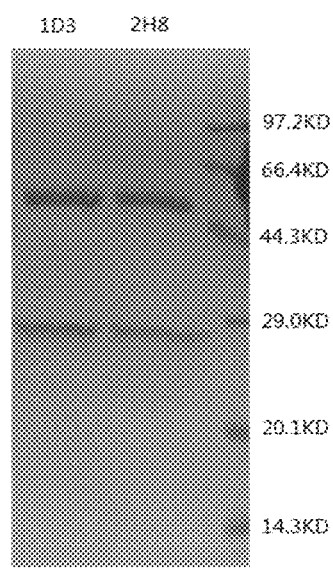
FIG. 2 shows purified recombinant monoclonal antibodies 1D3 and 2H8 (human IgG1 type)

The expression plasmids pIH-1D3 and pIK-1D3 were mixed in equimolar ratio, and pIH-2H8 and pIK-2H8 were mixed in equimolar ratio, transfected into well-growed HEK-293F cells, respectively, and cultured at 37° C., 5% $CO_2$ and 125 rpm for 7 days on a shaker. The culture was centrifuged at 4000 rpm for 10 min, the precipitate was discarded, and the supernatant was collected, and filtered through a 0.45 μm filter. The processed sample was affinity-purified through a protein A (purchased from GE) affinity column, thereby finally obtaining the purified recombinant monoclonal antibodies 1D3 and 2H8 (identification results are shown in FIG. 2).

Example 4

Affinity of Monoclonal Antibody for Human proBDNF Precursor Protein

Figure 3:
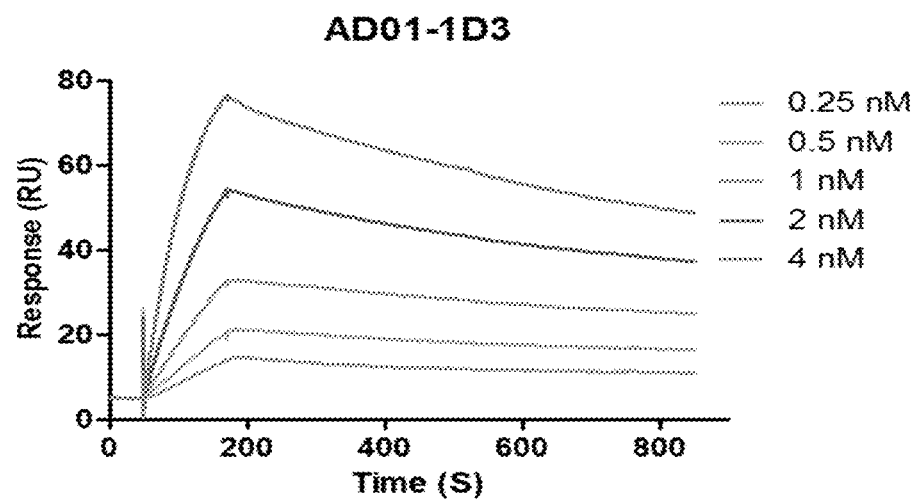
FIG. 3 is a kinetic curve of 1D3 in a Biacore affinity determination experiment.
Figure 4:
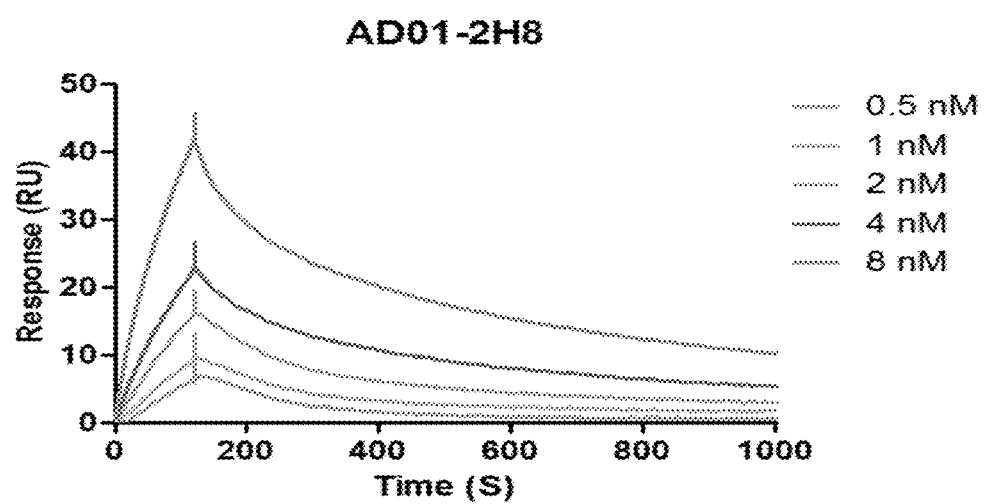
FIG. 4 is a kinetic curve of 2H8 in a Biacore affinity determination experiment.

The affinity and kinetic parameters of the 1D3 and 2H8 monoclonal antibodies were measured by the capture method using Biacore T200 system (purchased from GE), respectively. The system was manipulated according to the instructions, human proBDNF precursor protein was used at a concentration of 0.25 nM, 0.5 nM, 1 nM, 2 nM, 4 nM, and 8 nM, respectively. The Biacore T200 evaluation software was used to evaluate the resulting action curve and calculate the affinity KD value. FIGS. 3 and 4 show the kinetic curves of monoclonal antibodies 1D3 and 2H8 in Biacore affinity determination assay, respectively.

The binding data of 1D3 and 2H8 monoclonal antibodies to human proBDNF precursor protein are summarized in Table 1, respectively.

TABLE 1

Affinity parameters of 1D3 and 2H8 monoclonal antibodies for human proBDNF precursor protein

| Antibody sample | ka (1/Ms) | kd (1/s) | KD (M) |
|---|---|---|---|
| 1D3 monoclonal antibody | 5.256E+06 | 7.994E−04 | 1.521E−10 |
| 2H8 monoclonal antibody | 3.103E+06 | 5.940E−03 | 1.914E−09 |

Example 5

Experiment of Treating Experimental Autoimmune Encephalomyelitis (EAE) by using 2H8 and 1D3

Female C57BL/6 mice of SPF grade (6-8 weeks, weighing 18-20 g) were used in this experimant.

Preparation of EAE model: MOG35-55 (3 mg/ml)/IFA (H37RA 4 mg/ml) was completely emulsified, and subcutaneously injected at the left and right sides of the upper back and the left side of the tail root of the mouse with a dosage of 150 μl/mouse. At the same time, pertussis toxin PTX (0.5 μg/100 μl) was intraperitoneally injected at a dosage of 50 μl mouse, and the same dose of PTX was injected again 48 hours later. On the day 7, MOG35-55 (3 mg/ml)/IFA (H37RA 2 mg/ml) were given through subcutaneous injections to immunize mice at the left and right sides of the lower back and the right side of the tail root with a dosage of 150 μl/mouse.

20 mice were randomly divided into a fully human IgG control antibody group and 2H8 monoclonal antibody intervention group. In the cognate IgG control antibody group, fully human IgG control antibody was intraperitoneally injected (0.2 ml per time) on days 17, 19, and 23 after EAE modeling. In the 2H8 monoclonal antibody intervention group, 200 μL of 2H8 monoclonal antibody was intraperitoneally injected (5 mg/kg per time) on days 17, 19 and 23 after modeling.

The mice in the blank control group and the experimental group were scored daily with the EAE model clinical scoring standard as follows: 0 points, no clinical symptoms; 0.5 points, tail weakness; 1 point, tail paralysis; 2 points, coordinated movement disappeared; 2.5 points, unilateral hind limb paralysis; 3 points, bilateral hind limb paralysis; 3.5 points, bilateral hind limb paralysis with forelimb weakness; 4 points, forelimb paralysis; 5 points, dying or dead. Dead rats will be scored 5 points on the day of death, and will not be scored the next day.

Figure 5A:
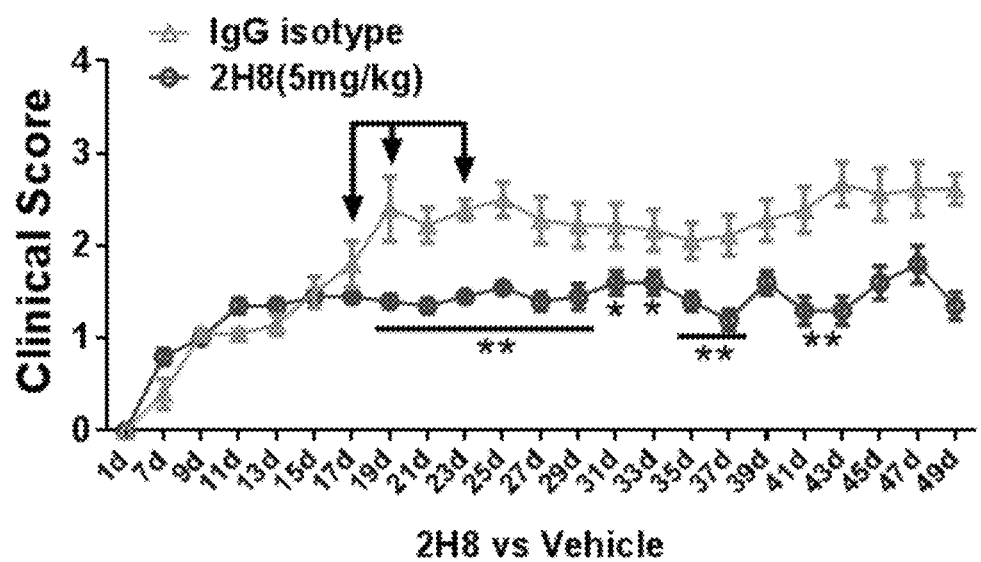
FIG. 5A is an experiment of treating experimental autoimmune encephalomyelitis (EAE) by using 2H8.
Figure 5B:
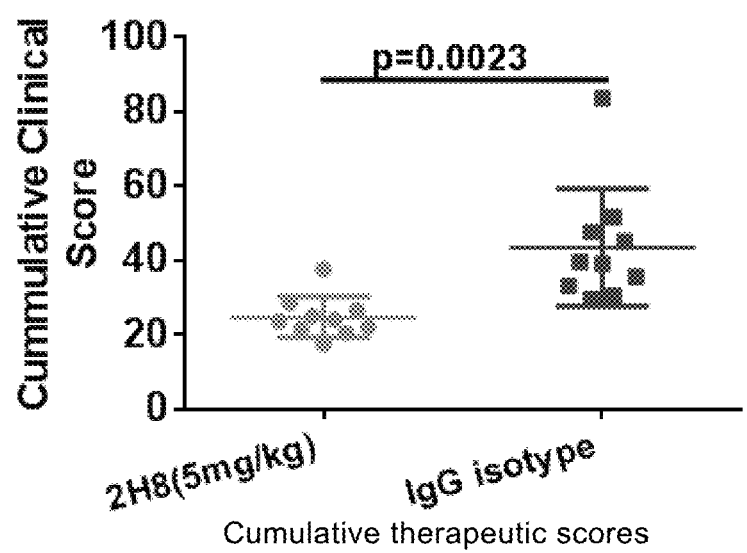
FIG. 5B is a cumulative treatment score of treating EAE by using 2H8.

The results are shown in FIGS. 5A and 5B. The EAE mice given the cognate control antibody showed a significant increase in clinical score 17 days after modeling, and the clinical score exceeded 2 points, and maintained until 49 days after modeling; and the clinical scores of EAE mice given 2H8 monoclonal antibodies were less than 1.5 from 17 to 49 days after modeling. Cumulative clinical scores showed that the cumulative clinical scores of EAE mice treated with cognate control antibodies (43.45±5.009 points) were significantly higher than the clinical scores (24.65±1.282 points) of EAE mice treated with 2H8 clones, suggesting that 2H8 clones have improved clinical symptoms of EAE mice.

Figure 6A:
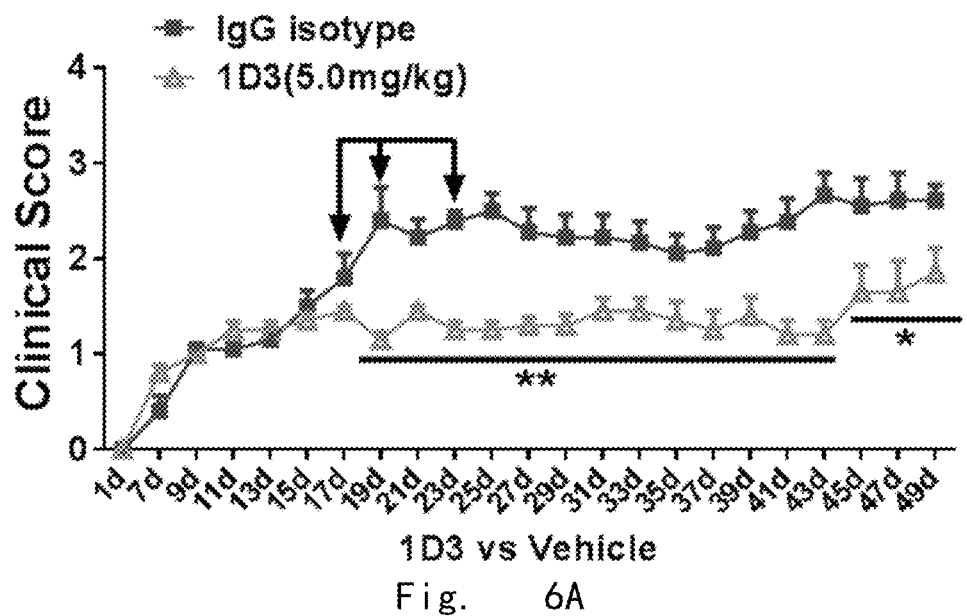
FIG. 6A is an experiment of treating experimental autoimmune encephalomyelitis (EAE) by using 1D3.
Figure 6B:
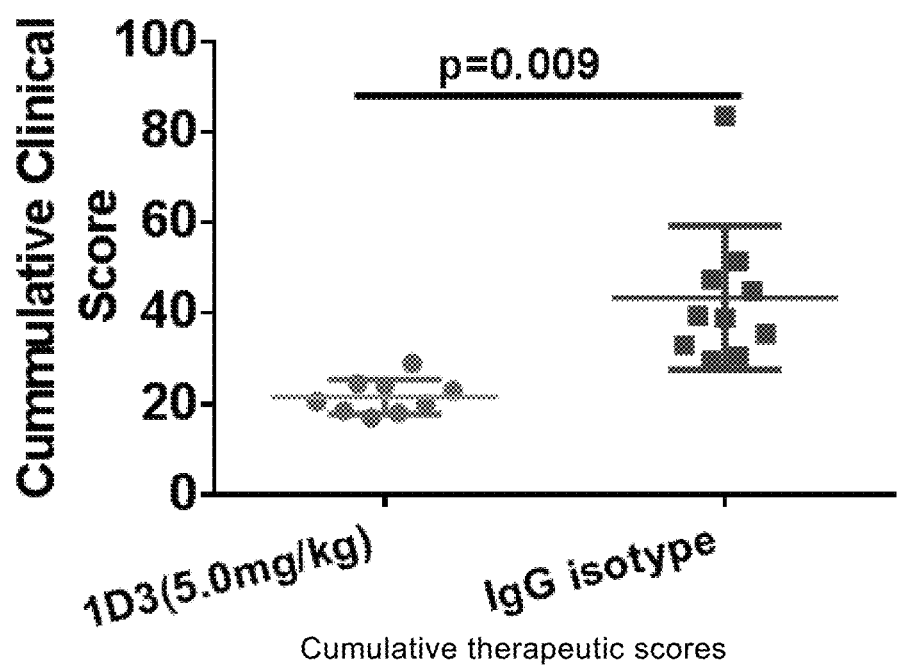
FIG. 6B is a cumulative treatment score of treating EAE by using 1D3.

According to the above operation of this example, antibody 1D3 was subjected to EAE model clinical score, and the results are shown in FIGS. 6A and 6B. Compared with the cognate IgG control antibody intervention group, the clinical score of EAE mice in the 1D3 clone intervention group was significantly reduced; the cumulative clinical treatment score of the 1D3 treatment group was 21.65±1.734, while the cognate control IgG antibody group was 43.45±5.009, suggesting that 1D3 can significantly reduce the progress of EAE mice.

Example 6

Effect of proBDNF Antibodies on Expression of Inflammatory Factors in Early Onset of EAE Mice The EAE modeling was performed according to Example 5. The experimental groups were: (1) control (con) group; (2) only Ab-proBDNF monoclonal antibody (Ab-proB) group: 1 day before modeling group, 5 mg/kg of Ab-proBDNF (1D3) monoclonal antibody was given; (3) EAE modeling+administration of cognate IgG antibody control (EAE) group; (4) EAE modeling+administration of Ab-proBDNF monoclonal antibody (EAE+Ab-proB) group. QPCR method was used to detect the expression of disease-related genes in spinal cord and spleen in each group, and the results are shown in FIG. 7.

Figure 7A:
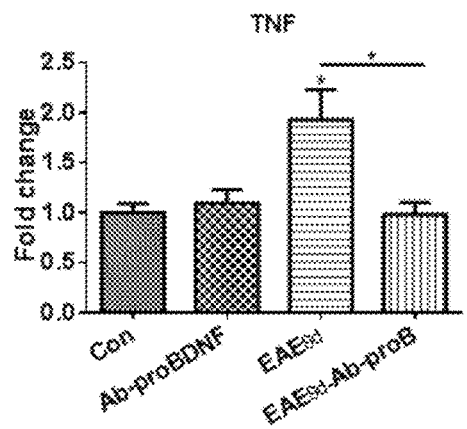
FIG. 7A shows the expression of the gene of inflammatory factor TNF-α.

FIG. 7A shows the expression of the inflammatory factor TNF-α gene. Compared with the control group, the expression of TNF-α in the Ab-proB group was substatially similar, while the expression of TNF-α in the EAE group was significantly higher than that in the control group, indicating that the proBDNF antibody has an intervention and prevention effect on early inflammation. Compared with the EAE group, the levels of TNF-α mRNA in the EAE+Ab-proB group were significantly reduced, and there was no significant difference compared with the control group, indicating that the administration of the 1D3 monoclonal antibody can significantly reduce the level of TNF-α, which means that proBDNF antibodies have anti-inflammatory effects.

Figure 7B:
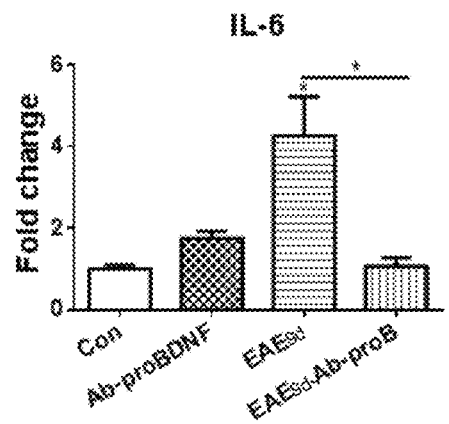
FIG. 7B shows the effect of Ab-proB on interleukin (IL)-6 in the spleen of EAE mice.
Figure 7C:
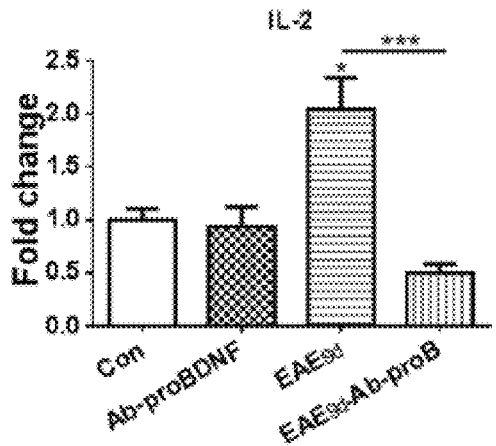
FIG. 7C shows the effect of Ab-proB on IL-2 in the spleen of EAE mice.
Figure 7D:
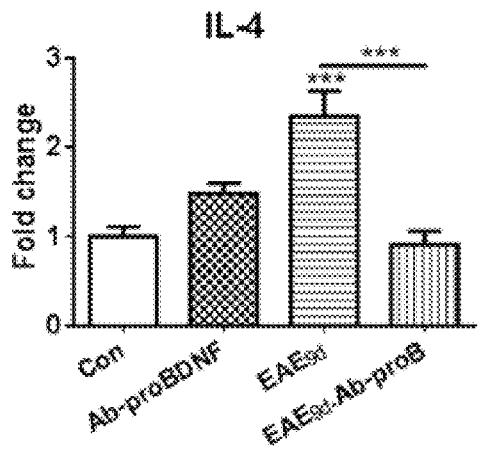
FIG. 7D shows the effect of Ab-proB on IL-4 in the spleen of EAE mice.

FIGS. 7B, 7C, and 7D show the effects of Ab-proB on IL-6, IL-2, and IL-4 in spleens of EAE mice, respectively. The results showed that compared with the control group, there was no significant difference in IL-6, IL-2, and IL-4 gene expression in the Ab-proB group, while the expression of TNF-α in the EAE group was significantly higher than that in the control group, indicating that ProBDNF antibody can intervene and prevent early inflammation. Compared with the control group, the expression of IL-6, IL-2, and IL-4 genes in the spleen in EAE group was significantly up-regulated. After 1D3 was given (EAE+Ab-proB group), IL-6, IL-2, and IL-4 gene levels were significantly lower than those in the EAE group. These results indicated that the administration of the proBDNF antibody can inhibit the early up-regulation of IL-6, IL-2, IL-4 mRNA levels in the spleen of EAE, which means that proBDNF antibody has anti-inflammatory effects.

Example 7

Antibody Epitope Binding Experiments

Western blot results showed that antibodies 1D3 and 2H8 can bind denatured huBDNFpro, suggesting that the binding epitopes of both antibodies are likely to be linear. huBDNFpro was divided into two peptide fragments (E1, E2) or three peptide fragments (E3, E4, E5), the amino acid sequences of which are listed as follows:

E1: pmkeanirgqgglaypgvrthgtlesvngpkagsrgltsladtfehmieelldedq (SEQ ID NO: 40)

E2: kvrpneennkdadlytsrvmlssqvpleppllflleeyknyldaanmsmrvah (SEQ ID NO: 41)

E3: pmkeanirgqgglaypgvrthgtlesvngpkagsrgl (SEQ ID NO: 42)

E4: tsladtfehmieelldedqkvrpneennkdadlytsr (SEQ ID NO: 43)

E5: vmlssqvpleppllflleeyknyldaanmsmrvah (SEQ ID NO: 44).

Figure 8:
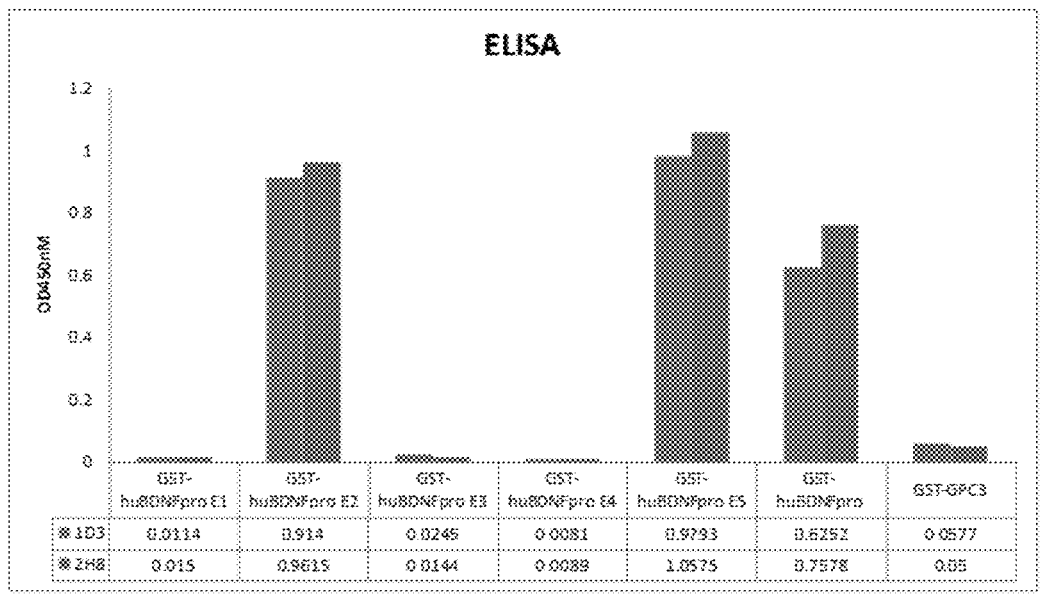
FIG. 8 shows the ELISA results of 1D3 and 2H8 with polypeptide E2 and polypeptide E5.

The five peptide fragments were fused with GST, expressed and purified. Binding of antibodies 1D3 and 2H8 was detected by ELISA. The results are shown in FIG. 8. Antibodies 1D3 and 2H8 can bind the full length GST-huBDNFpro, GST-huBDNFpro-E2 peptide fragment, and GST-huBDNFpro-E5 peptide fragment, suggesting that the binding epitopes of both antibodies are located within 36 amino acids of E5 peptide fragment.

Example 8

Antibody Epitope Binding Experiments

Figure 9:
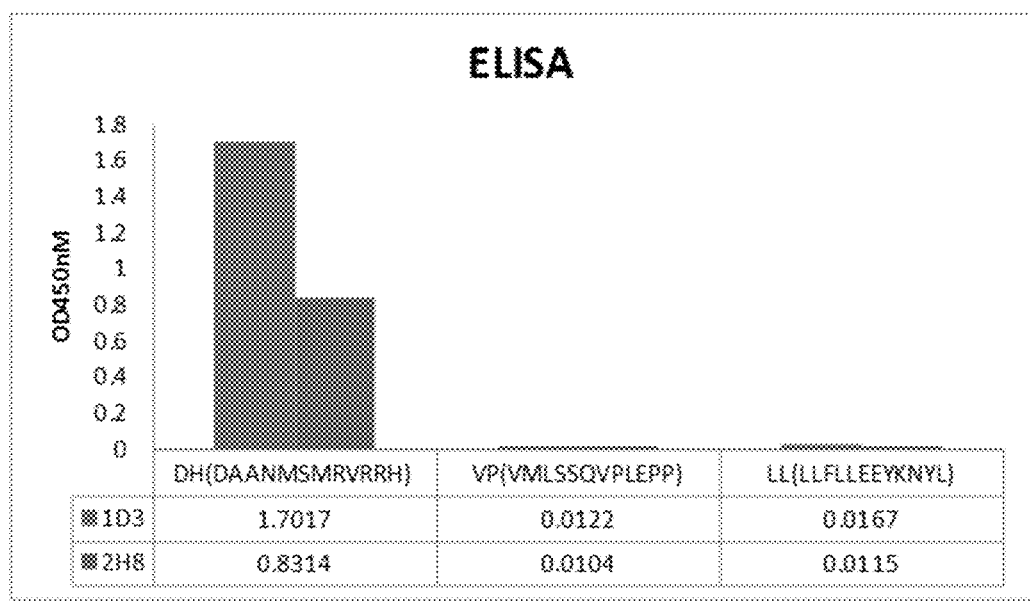
FIG. 9 shows the results of ELISA of 1D3 and 2H8 with polypeptide DH.

The E5 peptide fragment was further trisection-divided into three peptide fragments containing 12 amino acids, which were VP peptide fragment (VMLSSQVPLEPP, SEQ ID NO: 45), LL peptide fragment (LLFLLEEYKNYL, SEQ ID NO: 46), and DH peptide fragment (DAANMSMRVRRH, SEQ ID NO: 47). Biotinylated VP peptide fragment, LL peptide fragment and DH peptide fragment were synthesized in vitro by Jill Biochemical (Shanghai) Co., Ltd. and antibody binding was detected by ELISA. The results are shown in FIG. 9. The antibodies 1D3 strongly bound DH peptide fragment, 2H8 weakly bound DH peptide fragment, and did not bind to the other two peptide fragments, suggesting that the epitope of antibody 1D3 is on the DH peptide fragment and the epitope of 2H8 is near the DH peptide fragment.

The sequences involved in the present invention are summarized in the following table

| Name | SEQ ID NO | Sequence |
|---|---|---|
| 1D3, HCDR1 | 1 | GYDMH |
| 1D3, HCDR2 | 2 | GLGMEGDSYYSASVKG |
| 1D3, HCDR3 | 3 | DVHGFDV |
| 1D3, LCDR1 | 4 | RSSQSLLYSNGYTYLD |
| 1D3, LCDR2 | 5 | MGSNRAS |
| 1D3, LCDR3 | 6 | MQALQTPLT |

| Name | SEQ ID NO | Sequence |
|---|---|---|
| 1D3, VH | 7 | QVQLVESGGGLIQPGGSMRLSCAASGFSLSGYDMHWVRQIAGKGL EWVAGLGMEGDSYYSASVKGRFTISRQDAKNSLYLEMKDLGGGD TAVYYCLRDVHGFDVWGQGTTVTVSS |
| 1D3, VL | 8 | DVVMTQSPLSLPVTPGEPASISCRSSQSLLYSNGYTYLDWYLQRPG QSPQLLIYMGSNRASGVPDRFSGSGSGTDFTLKISRVEAEDVGVYY CMQALQTPLTFGGGTKLEIKR |
| 1D3, heavy chain | 9 | QVQLVESGGGLIQPGGSMRLSCAASGFSLSGYDMHWVRQIAGKG LEWVAGLGMEGDSYYSASVKGRFTISRQDAKNSLYLEMKDLGGG DTAVYYCLRDVHGFDVWGQGTTVTVSSASTKGPSVFPLAPCSRST SESTAALGCLVKDYFPEPVTVSWNSGALTSGVHTFPAVLQSSGLY SLSSVVTVPSSSLGTKTYTCNVDHKPSNTKVDKRVESKYGPPCPSC PAPEFLGGPSVFLFPPKPKDTLMISRTPEVTCVVVDVSQEDPEVQF NWYVDGVEVHNAKTKPREEQFNSTYRVVSVLTVLHQDWLNGKE YKCKVSNKGLPSSIEKTISKAKGQPREPQVYTLPPSQEEMTKNQV SLTCLVKGFYPSDIAVEWESNGQPENNYKTTPPVLDSDGSFFLYS RLTVDKSRWQEGNVFSCSVMHEALHNHYTQKSLSLSPGK |
| 1D3, light chain | 10 | DVVMTQSPLSLPVTPGEPASISCRSSQSLLYSNGYTYLDWYLQR PGQSPQLLIYMGSNRASGVPDRFSGSGSGTDFTLKISRVEAEDV GVYYCMQALQTPLTFGGGTKLEIKRTVAAPSVFIFPPSDEQLKS GTASVVCLLNNFYPREAKVQWKVDNALQSGNSQESVTEQDSK DSTYSLSSTLTLSKADYEKHKVYACEVTHQGLSSPVTKSFNRG EC |
| 2H8, HCDR1 | 11 | SYGMH |
| 2H8, HCDR2 | 12 | VISGSGDSTYYAESVKG |
| 2H8, HCDR3 | 13 | GILTGYVFDY |
| 2H8, LCDR1 | 14 | RSSQSLVSNDGNTYLN |
| 2H8, LCDR2 | 15 | MVSKWDS |
| 2H8, LCDR3 | 16 | MQSTHWPPT |
| 2H8, VH | 17 | EVQLVETGGGLVQPGGSLRLSCAASGFTFSSYGMHWVRQAPGK GLEWVSVISGSGDSTYYAESVKGRFTISRDNARNTVYLQMNSLR AEDTAVYYCASGILTGYVFDYWGKGTMVTVSS |
| 2H8, VL | 18 | DVVMTQSPLSLPVTLGQPASISCRSSQSLVSNDGNTYLNWFQQR PGQPPRRLIYMVSKWDSGVPDRFSGSGSGTDFTLRISRVEAEDV GVYYCMQSTHWPPTFGGGTKLEIKR |
| 2H8, heavy chain | 19 | EVQLVETGGGLVQPGGSLRLSCAASGFTFSSYGMHWVRQAPGKGL EWVSVISGSGDSTYYAESVKGRFTISRDNARNTVYLQMNSLRAEDT AVYYCASGILTGYVFDYWGKGTMVTVSSASTKGPSVFPLAPCSRST SESTAALGCLVKDYFPEPVTVSWNSGALTSGVHTFPAVLQSSGLYS LSSVVTVPSSSLGTKTYTCNVDRKPSNTKVDKRVESKYGPPCPSCP APEFLGGPSVFLFPPKPKDTLMISRTPEVTCVVVDVSQEDPEVQFN WYVDGVEVHNAKTKPREEQFNSTYRVVSVLTVLHQDWLNGKEY KCKVSNKGLPSSIEKTISKAKGQPREPQVYTLPPSQEEMTKNQVSL TCLVKGFYPSDIAVEWESNGQPENNYKTTPPVLDSDGSFFLYSRL TVDKSRWQEGNVFSCSVMHEALHNHYTQKSLSLSPGK |
| 2H8, light chain | 20 | DVVMTQSPLSLPVTLGQPASISCRSSQSLVSNDGNTYLNWFQQR PGQPPRRLIYMVSKWDSGVPDRFSGSGSGTDFTLRISRVEAEDV GVYYCMQSTHWPPTFGGGTKLEIKRTVAAPSVFIFPPSDEQLKS GTASVVCLLNNFYPREAKVQWKVDNALQSGNSQESVTEQDSK DSTYSLSSTLTLSKADYEKHKVYACEVTHQGLSSPVTKSFNRGEC |
| 1D3, scFv | 21 | QVQLVESGGGLIQPGGSMRLSCAASGFSLSGYDMHWVRQIAGK GLEWVAGLGMEGDSYYSASVKGRFTISRQDAKNSLYLEMKDL GGGDTAVYYCLRDVHGFDVWGQGTTVTVSSGGGGSGGGGSG GGGSDVVMTQSPLSLPVTPGEPASISCRSSQSLLYSNGYTYLDW YLQRPGQSPQLLIYMGSNRASGVPDRFSGSGSGTDFTLKISRVE AEDVGVYYCMQALQTPLTFGGGTKLEIKR |
| 1D3, scFv, nucleotide sequence | 22 | CAGGTGCAGCTGGTGGAGTCTGGGGGAGGCCTGATAC AGCCGGGGGGGTCGATGAGACTCTCCTGTGCAGCCTC TGGATTCAGCCTCAGTGGATATGACATGCACTGGGTC CGCCAAATTGCGGGAAAAGGTCTGGAGTGGGTCGCCG GTCTTGGGATGGAAGGTGACTCATATTATTCAGCCTCC |

| Name | SEQ ID NO | Sequence |
|---|---|---|
| | | GTGAAGGGCCGATTCACCATCTCCAGACAAGATGCCA<br>AGAATTCCCTGTATCTTGAAATGAAGGACCTGGGAGG<br>CGGGGACACGGCTGTCTATTACTGTCTAAGAGATGTC<br>CACGGATTCGACGTCTGGGGCCAAGGGACCACGGTC<br>ACCGTCTCGAGTGGTGGAGGCGGTTCAGGCGGAGGTG<br>GTTCTGGCGGTGGCGGATCGGATGTTGTGATGACTCAG<br>TCTCCACTCTCCCTGCCCGTCACCCCTGGAGAGCCGGC<br>CTCCATCTCCTGCAGGTCTAGTCAGAGCCTCCTGTATA<br>GTAATGGATACACCTATTTGGATTGGTACCTGCAGAG<br>GCCAGGGCAGTCTCCACAGCTCCTGATCTATATGGG<br>TTCTAATCGGGCCTCCGGGGTCCCTGACAGGTTCAGT<br>GGCAGTGGATCAGGCACAGATTTTACACTGAAAATCA<br>GCAGAGTGGAGGCTGAGGATGTTGGGGTTTATTACTG<br>CATGCAAGCTCTACAAACTCCCCTCACTTTCGGCGGA<br>GGGACCAAGCTGGAGATCAAACGT |
| 2H8, scFv | 23 | EVQLVETGGGLVQPGGSLRLSCAASGFTFSSYGMHWVR<br>QAPGKGLEWVSVISGSGDSTYYAESVKGRFTISRDNARN<br>TVYLQMNSLRAEDTAVYYCASOLTGYVFDYWGKGTM<br>VTVSSGGGGSGGGGSGGGGSDVVMTQSPLSLPVTLGQP<br>ASISCRSSQSLVSNDGNTYLNWFQQRPGQPPRRLIYMVS<br>KWDSGVPDRFSGSGSGTDFTLRISRVEAEDVGVYYCMQ<br>STHWPPTFGGGTKLEIKR |
| 2H8, scFv, nucleotide sequence | 24 | GAGGTGCAGCTGGTGGAGACTGGGGGCGGCTTGGTCC<br>AGCCTGGGGGGTCCCTGAGACTCTCCTGTGCAGCGTCT<br>GGATTCACCTTCAGTAGCTATGGCATGCACTGGGTCCG<br>CCAGGCTCCAGGGAAGGGGCTGGAGTGGGTCTCAGTT<br>ATTAGTGGTAGTGGTGATAGTACATACTACGCAGAGTC<br>CGTGAAGGGCCGCTTCACCATCTCCAGAGACAATGCCA<br>GGAACACGGTGTATCTGCAAATGAACAGTCTGAGAGCC<br>GAGGACACGGCTGTATATTATTGTGCAAGTGGCATTTTG<br>ACTGGTTATGTATTTGACTATTGGGGCAAAGGGACAATG<br>GTCACCGTCTCGAGTGGTGGAGGCGGTTCAGGCGGAGG<br>TGGTTCTGGCGGTGGCGGATCGGATGTTGTGATGACTCAG<br>TCTCCACTCTCCCTGCCCGTCACCCTTGGACAGCCGGCCT<br>CCATCTCCTGCAGGTCTAGTCAAAGCCTCGTATCCAATG<br>ATGGAAACACCTACTTGAATTGGTTTCAGCAGAGGCCAG<br>GCCAACCTCCAAGGCGCCTAATTTATATGGTTTCTAAGT<br>GGGACTCTGGGGTCCCAGACAGATTCAGCGGCAGTGGG<br>TCAGGCACTGATTTCACACTGAGAATCAGCAGGGTGGA<br>GGCTGAGGATGTTGGGGTTTATTACTGCATGCAAAGTAC<br>ACACTGGCCTCCCACTTTCGGCGGAGGGACCAAGCTGG<br>AGATCAAACGT |
| Primer PROBDNF-F | 25 | GCGAATTCCCCATGAAAGAAGCAAACATCC |
| PROBDNF-R | 26 | CCGCTCGAGTTATCTTCCCCTTTTAATGGTCAATG |
| Human proBDNF gene sequence | 27 | Gccccatgaaagaagcaaacatccgaggacaaggtggcttggcctacccaggtgtgc<br>ggacccatgggaCtctggagagcgtgaatgggcccaaggcaggttcaagaggcttgac<br>atcattggctgacactttcgaacacatGatagaagagctgttggatgaggaccagaaagtt<br>cggcccaatgaagaaaacaataaggacgcagacttgtaCacgtccagggtgatgctcag<br>tagtcaagtgcctttggagcctcctcttctctttctgctggaggaatacaaaaat-<br>tacctagat<br>gctgcaaacatgtccatgagggtccggcgc |
| Primer BDNFproVF1 | 28 | GCTGGCTAGCACCCATGAAAGAAGCAAACATCCGAG |
| Primer BDNFproVR1 | 29 | CCGCTCGAGGTGGCGCCGGACCCTCATG |
| Primer pair 1D3-HF | 30 | gcctttcctggthcctgtctcaggtgcagctggtggag |
| Primer pair 1D3-HR | 31 | ATGGGCCCTTGGTGGAGGCACTCGAGACGGTGACCGTG |
| Primer pair HF1F | 32 | ggctaactagagaacccactgc |
| Primer pair HF1R | 33 | AGACAGGAAACCAGGAAAGGC |

| Name | SEQ ID NO | Sequence |
|---|---|---|
| Primer pair HF3F | 34 | gcctccaccaagggcccatc |
| Primer pair HF3R | 35 | gacaatcttagcgcagaagtc |
| Primer pair 1D3-LF | 36 | ctttggtttccaggtgcaagatgtgatgttgtgatgactcagtctcc |
| Primer pair 1D3-LR | 37 | CACCGTACGTTTGATCTCCAGCTTGG |
| Primer pair LF1F | 38 | ggctaactagagaacccactgc |
| LF1R | 39 | ACATCTTGCACCTGGAAACCAAAG |
| E1 | 40 | pmkeanirgqgglaypgvrthgtlesvngpkagsrgltsladtfehmieelldedq |
| E2 | 41 | kvrpneennkdadlytsrvmlssqvpleppllflleeyknyldaanmsmvrrh |
| E3 | 42 | pmkeanirgqgglaypgvrthgtlesvngpkagsrgl |
| E4 | 43 | tsladtfehmieelldedqkvrpneennkdadlytsr |
| E5 | 44 | vmlssqvpleppllflleeyknyldaanmsmrvrrh |
| VP | 45 | VMLSSQVPLEPP |
| LL | 46 | LLFLLEEYKNYL |
| DH | 47 | DAANMSMRVRRH |

All documents mentioned in the present invention are incorporated by reference in this application, as if each document was individually incorporated by reference. In addition, it should be understood that after reading the above teaching content of the present invention, a skilled person in the art can make various changes or modifications to the present invention, and these equivalent forms also fall within the scope defined by the claims appended to this application.

The invention claimed is:

1. An antibody or an antigen-binding fragment thereof that specifically binds to a precursor of brain-derived neurotrophic factor (pro-BDNF), wherein the antibody or antigen-binding fragment thereof comprises:
   (a) a heavy chain variable region comprising a CDR1 as shown in SEQ ID NO: 1, a CDR2 as shown in SEQ ID NO: 2, and a CDR3 as shown in SEQ ID NO: 3, and a light chain variable region comprising a CDR1 as shown in SEQ ID NO: 4, a CDR2 as shown in SEQ ID NO: 5, and a CDR3 as shown in SEQ ID NO: 6; or
   (b) a heavy chain variable region comprising a CDR1 as shown in SEQ ID NO: 11, a CDR2 as shown in SEQ ID NO: 12, and a CDR3 as shown in SEQ ID NO: 13, and a light chain variable region comprising a CDR1 as shown in SEQ ID NO: 14, a CDR2 as shown in SEQ ID NO: 15, and a CDR3 as shown in SEQ ID NO: 16.

2. An antibody or an antigen-binding fragment thereof that specifically binds to pro-BDNF, wherein the antibody or antigen-binding fragment thereof comprises:
   (a) a heavy chain variable region as shown in SEQ ID NO: 7 and a light chain variable region as show in SEQ ID NO: 8;
   (b) the amino acid sequence of SEQ ID NO: 21;
   (c) a heavy chain variable region as shown in SEQ ID NO: 17 and a light chain variable region as shown in SEQ ID NO: 18; or
   (d) the amino acid sequence of SEQ ID NO: 23.

3. The antibody of claim 1, wherein the antibody is obtained by immunizing an animal or by screening a phage library using a polypeptide comprising an amino acid sequence as shown in SEQ ID NO: 41.

4. A pharmaceutical composition comprising the antibody of claim 1.

5. The pharmaceutical composition according to claim 4, further comprising at least one pharmaceutically acceptable excipient, diluent, or a carrier.

* * * * *

```
                        SEQUENCE LISTING

<160> NUMBER OF SEQ ID NOS: 47

<210> SEQ ID NO 1
<211> LENGTH: 5
<212> TYPE: PRT
<213> ORGANISM: Artificial Sequence
<220> FEATURE:
<223> OTHER INFORMATION: 1D3, HCDR1

<400> SEQUENCE: 1

Gly Tyr Asp Met His
1               5

<210> SEQ ID NO 2
<211> LENGTH: 16
<212> TYPE: PRT
<213> ORGANISM: Artificial Sequence
<220> FEATURE:
<223> OTHER INFORMATION: 1D3, HCDR2

<400> SEQUENCE: 2

Gly Leu Gly Met Glu Gly Asp Ser Tyr Tyr Ser Ala Ser Val Lys Gly
1               5                   10                  15

<210> SEQ ID NO 3
<211> LENGTH: 7
```

```
<212> TYPE: PRT
<213> ORGANISM: Artificial Sequence
<220> FEATURE:
<223> OTHER INFORMATION: 1D3, HCDR3

<400> SEQUENCE: 3

Asp Val His Gly Phe Asp Val
1               5

<210> SEQ ID NO 4
<211> LENGTH: 16
<212> TYPE: PRT
<213> ORGANISM: Artificial Sequence
<220> FEATURE:
<223> OTHER INFORMATION: 1D3, LCDR1

<400> SEQUENCE: 4

Arg Ser Ser Gln Ser Leu Leu Tyr Ser Asn Gly Tyr Thr Tyr Leu Asp
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: 1D3, LCDR2

<400> SEQUENCE: 5

Met Gly Ser Asn Arg Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: 1D3, LCDR3

<400> SEQUENCE: 6

Met Gln Ala Leu Gln Thr Pro Leu Thr
1               5

<210> SEQ ID NO 7
<211> LENGTH: 115
<212> TYPE: PRT
<213> ORGANISM: Artificial Sequence
<220> FEATURE:
<223> OTHER INFORMATION: 1D3, VH

<400> SEQUENCE: 7

Gln Val Gln Leu Val Glu Ser Gly Gly Leu Ile Gln Pro Gly Gly
1               5                   10                  15

Ser Met Arg Leu Ser Cys Ala Ala Ser Gly Phe Ser Leu Ser Gly Tyr
                20                  25                  30

Asp Met His Trp Val Arg Gln Ile Ala Gly Lys Gly Leu Glu Trp Val
            35                  40                  45

Ala Gly Leu Gly Met Glu Gly Asp Ser Tyr Tyr Ser Ala Ser Val Lys
        50                  55                  60

Gly Arg Phe Thr Ile Ser Arg Gln Asp Ala Lys Asn Ser Leu Tyr Leu
65                  70                  75                  80

Glu Met Lys Asp Leu Gly Gly Gly Asp Thr Ala Val Tyr Tyr Cys Leu
                85                  90                  95

Arg Asp Val His Gly Phe Asp Val Trp Gly Gln Gly Thr Thr Val Thr
            100                 105                 110
```

Val Ser Ser
        115

<210> SEQ ID NO 8
<211> LENGTH: 113
<212> TYPE: PRT
<213> ORGANISM: Artificial Sequence
<220> FEATURE:
<223> OTHER INFORMATION: 1D3, VL

<400> SEQUENCE: 8

Asp Val Val Met Thr Gln Ser Pro Leu Ser Leu Pro Val Thr Pro Gly
1               5                   10                  15

Glu Pro Ala Ser Ile Ser Cys Arg Ser Gln Ser Leu Leu Tyr Ser
            20                  25                  30

Asn Gly Tyr Thr Tyr Leu Asp Trp Tyr Leu Gln Arg Pro Gly Gln Ser
        35                  40                  45

Pro Gln Leu Leu Ile Tyr Met Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Leu Glu Ile Lys
            100                 105                 110

Arg

<210> SEQ ID NO 9
<211> LENGTH: 442
<212> TYPE: PRT
<213> ORGANISM: Artificial Sequence
<220> FEATURE:
<223> OTHER INFORMATION: 1D3, heavy chain

<400> SEQUENCE: 9

Gln Val Gln Leu Val Glu Ser Gly Gly Gly Leu Ile Gln Pro Gly Gly
1               5                   10                  15

Ser Met Arg Leu Ser Cys Ala Ala Ser Gly Phe Ser Leu Ser Gly Tyr
            20                  25                  30

Asp Met His Trp Val Arg Gln Ile Ala Gly Lys Gly Leu Glu Trp Val
        35                  40                  45

Ala Gly Leu Gly Met Glu Gly Asp Ser Tyr Tyr Ser Ala Ser Val Lys
    50                  55                  60

Gly Arg Phe Thr Ile Ser Arg Gln Asp Ala Lys Asn Ser Leu Tyr Leu
65                  70                  75                  80

Glu Met Lys Asp Leu Gly Gly Gly Asp Thr Ala Val Tyr Tyr Cys Leu
                85                  90                  95

Arg Asp Val His Gly Phe Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

```
Leu Tyr Ser Leu Ser Ser Val Thr Val Pro Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Ser Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 10
<211> LENGTH: 219
<212> TYPE: PRT
<213> ORGANISM: Artificial Sequence
<220> FEATURE:
<223> OTHER INFORMATION: 1D3, light chain

<400> SEQUENCE: 10

Asp Val Val Met Thr Gln Ser Pro Leu Ser Leu Pro Val Thr Pro Gly
1               5                   10                  15

Glu Pro Ala Ser Ile Ser Cys Arg Ser Gln Ser Leu Leu Tyr Ser
            20                  25                  30

Asn Gly Tyr Thr Tyr Leu Asp Trp Tyr Leu Gln Arg Pro Gly Gln Ser
        35                  40                  45

Pro Gln Leu Leu Ile Tyr Met Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

```
Leu Gln Thr Pro Leu Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 11
<211> LENGTH: 5
<212> TYPE: PRT
<213> ORGANISM: Artificial Sequence
<220> FEATURE:
<223> OTHER INFORMATION: 2H8, HCDR1

<400> SEQUENCE: 11

Ser Tyr Gly Met His
1               5

<210> SEQ ID NO 12
<211> LENGTH: 17
<212> TYPE: PRT
<213> ORGANISM: Artificial Sequence
<220> FEATURE:
<223> OTHER INFORMATION: 2H8, HCDR2

<400> SEQUENCE: 12

Val Ile Ser Gly Ser Gly Asp Ser Thr Tyr Tyr Ala Glu Ser Val Lys
1               5                   10                  15

Gly

<210> SEQ ID NO 13
<211> LENGTH: 10
<212> TYPE: PRT
<213> ORGANISM: Artificial Sequence
<220> FEATURE:
<223> OTHER INFORMATION: 2H8, HCDR3

<400> SEQUENCE: 13

Gly Ile Leu Thr Gly Tyr Val Phe Asp Tyr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: 2H8, LCDR1

<400> SEQUENCE: 14

Arg Ser Ser Gln Ser Leu Val Ser Asn Asp Gly Asn Thr Tyr Leu Asn
1               5                   10                  15
```

<210> SEQ ID NO 15
<211> LENGTH: 7
<212> TYPE: PRT
<213> ORGANISM: Artificial Sequence
<220> FEATURE:
<223> OTHER INFORMATION: 2H8, LCDR2

<400> SEQUENCE: 15

Met Val Ser Lys Trp Asp Ser
1               5

<210> SEQ ID NO 16
<211> LENGTH: 9
<212> TYPE: PRT
<213> ORGANISM: Artificial Sequence
<220> FEATURE:
<223> OTHER INFORMATION: 2H8, LCDR3

<400> SEQUENCE: 16

Met Gln Ser Thr His Trp Pro Pro Thr
1               5

<210> SEQ ID NO 17
<211> LENGTH: 119
<212> TYPE: PRT
<213> ORGANISM: Artificial Sequence
<220> FEATURE:
<223> OTHER INFORMATION: 2H8, VH

<400> SEQUENCE: 17

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Ser Gly Ser Gly Asp Ser Thr Tyr Tyr Ala Glu Ser Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Arg Ala Glu Asp Thr Ala Val Tyr Tyr Cys
                85                  90                  95

Ala Ser Gly Ile Leu Thr Gly Tyr Val Phe Asp Tyr Trp Gly Lys Gly
            100                 105                 110

Thr Met Val Thr Val Ser Ser
        115

<210> SEQ ID NO 18
<211> LENGTH: 113
<212> TYPE: PRT
<213> ORGANISM: Artificial Sequence
<220> FEATURE:
<223> OTHER INFORMATION: 2H8, VL

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Ser Asn
            20                  25                  30

Asp Gly Asn Thr Tyr Leu Asn Trp Phe Gln Gln Arg Pro Gly Gln Pro
        35                  40                  45

```
Pro Arg Arg Leu Ile Tyr Met Val Ser Lys Trp Asp Ser Gly Val Pro
        50                  55                  60
Asp Arg Phe Ser Gly Ser Gly Ser Gly Thr Asp Phe Thr Leu Arg Ile
 65              70                  75                  80
Ser Arg Val Glu Ala Glu Asp Val Gly Val Tyr Tyr Cys Met Gln Ser
                 85                  90                  95
Thr His Trp Pro Pro Thr Phe Gly Gly Gly Thr Lys Leu Glu Ile Lys
            100                 105                 110
Arg
```

<210> SEQ ID NO 19
<211> LENGTH: 446
<212> TYPE: PRT
<213> ORGANISM: Artificial Sequence
<220> FEATURE:
<223> OTHER INFORMATION: 2H8, heavy chain

<400> SEQUENCE: 19

```
Glu Val Gln Leu Val Glu Thr Gly Gly Gly Leu Val Gln Pro Gly Gly
 1               5                  10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
         35                  40                  45
Ser Val Ile Ser Gly Ser Gly Asp Ser Thr Tyr Tyr Ala Glu Ser Val
     50                  55                  60
Lys Gly Arg Phe Thr Ile Ser Arg Asp Asn Ala Arg Asn Thr Val Tyr
 65                  70                  75                  80
Leu Gln Met Asn Ser Leu Arg Ala Glu Asp Thr Ala Val Tyr Tyr Cys
                 85                  90                  95
Ala Ser Gly Ile Leu Thr Gly Tyr Val Phe Asp Tyr Trp Gly Lys Gly
            100                 105                 110
Thr Met Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
    210                 215                 220
Cys Pro Ser Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
```

```
              290                 295                 300
Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 20
<211> LENGTH: 219
<212> TYPE: PRT
<213> ORGANISM: Artificial Sequence
<220> FEATURE:
<223> OTHER INFORMATION: 2H8, light chain

<400> SEQUENCE: 20

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Ser Asn
                20                  25                  30

Asp Gly Asn Thr Tyr Leu Asn Trp Phe Gln Gln Arg Pro Gly Gln Pro
            35                  40                  45

Pro Arg Arg Leu Ile Tyr Met Val Ser Lys Trp Asp Ser Gly Val Pro
50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Ser
                85                  90                  95

Thr His Trp Pro Pro Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
```

<210> SEQ ID NO 21
<211> LENGTH: 243
<212> TYPE: PRT
<213> ORGANISM: Artificial Sequence
<220> FEATURE:
<223> OTHER INFORMATION: 1D3, scFv

<400> SEQUENCE: 21

```
Gln Val Gln Leu Val Glu Ser Gly Gly Gly Leu Ile Gln Pro Gly Gly
1               5                   10                  15

Ser Met Arg Leu Ser Cys Ala Ala Ser Gly Phe Ser Leu Ser Gly Tyr
            20                  25                  30

Asp Met His Trp Val Arg Gln Ile Ala Gly Lys Gly Leu Glu Trp Val
        35                  40                  45

Ala Gly Leu Gly Met Glu Gly Asp Ser Tyr Tyr Ser Ala Ser Val Lys
    50                  55                  60

Gly Arg Phe Thr Ile Ser Arg Gln Asp Ala Lys Asn Ser Leu Tyr Leu
65                  70                  75                  80

Glu Met Lys Asp Leu Gly Gly Gly Asp Thr Ala Val Tyr Tyr Cys Leu
                85                  90                  95

Arg Asp Val His Gly Phe Asp Val Trp Gly Gln Gly Thr Thr Val Thr
            100                 105                 110

Val Ser Ser Gly Gly Gly Gly Ser Gly Gly Gly Gly Ser Gly Gly Gly
        115                 120                 125

Gly Ser Asp Val Val Met Thr Gln Ser Pro Leu Ser Leu Pro Val Thr
    130                 135                 140

Pro Gly Glu Pro Ala Ser Ile Ser Cys Arg Ser Gln Ser Leu Leu
145                 150                 155                 160

Tyr Ser Asn Gly Tyr Thr Tyr Leu Asp Trp Tyr Leu Gln Arg Pro Gly
                165                 170                 175

Gln Ser Pro Gln Leu Leu Ile Tyr Met Gly Ser Asn Arg Ala Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Met
    210                 215                 220

Gln Ala Leu Gln Thr Pro Leu Thr Phe Gly Gly Gly Thr Lys Leu Glu
225                 230                 235                 240

Ile Lys Arg
```

<210> SEQ ID NO 22
<211> LENGTH: 729
<212> TYPE: DNA
<213> ORGANISM: Artificial Sequence
<220> FEATURE:
<223> OTHER INFORMATION: 1D3, scFv, nucleotide sequence

<400> SEQUENCE: 22

```
caggtgcagc tggtggagtc tggggggaggc ctgatacagc cggggggggtc gatgagactc      60 tcctgtgcag cctctggatt cagcctcagt ggatatgaca tgcactgggt ccgccaaatt     120
gcgggaaaag gtctggagtg gtcgccggt cttgggatgg aaggtgactc atattattca     180
gcctccgtga aggccgatt caccatctcc agacaagatg ccaagaattc cctgtatctt     240
gaaatgaagg acctggagg cggggacacg gctgtctatt actgtctaag agatgtccac     300
```

```
ggattcgacg tctggggcca agggaccacg gtcaccgtct cgagtggtgg aggcggttca    360
ggcggaggtg gttctggcgg tggcggatcg gatgttgtga tgactcagtc tccactctcc    420
ctgcccgtca cccctggaga gccggcctcc atctcctgca ggtctagtca gagcctcctg    480
tatagtaatg gatacaccta tttggattgg tacctgcaga ggccagggca gtctccacag    540
ctcctgatct atatgggttc taatcgggcc tccggggtcc ctgacaggtt cagtggcagt    600
ggatcaggca cagattttac actgaaaatc agcagagtgg aggctgagga tgttggggtt    660
tattactgca tgcaagctct acaaactccc ctcactttcg gcggagggac caagctggag    720
atcaaacgt                                                           729
```

<210> SEQ ID NO 23
<211> LENGTH: 247
<212> TYPE: PRT
<213> ORGANISM: Artificial Sequence
<220> FEATURE:
<223> OTHER INFORMATION: 2H8, scFv

<400> SEQUENCE: 23

```
Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Ser Gly Ser Gly Asp Ser Thr Tyr Tyr Ala Glu Ser Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Arg Ala Glu Asp Thr Ala Val Tyr Tyr Cys
                85                  90                  95

Ala Ser Gly Ile Leu Thr Gly Tyr Val Phe Asp Tyr Trp Gly Lys Gly
            100                 105                 110

Thr Met Val Thr Val Ser Ser Gly Gly Gly Gly Ser Gly Gly Gly Gly
        115                 120                 125

Ser Gly Gly Gly Gly Ser Asp Val Val Met Thr Gln Ser Pro Leu Ser
    130                 135                 140

Leu Pro Val Thr Leu Gly Gln Pro Ala Ser Ile Ser Cys Arg Ser Ser
145                 150                 155                 160

Gln Ser Leu Val Ser Asn Asp Gly Asn Thr Tyr Leu Asn Trp Phe Gln
                165                 170                 175

Gln Arg Pro Gly Gln Pro Pro Arg Arg Leu Ile Tyr Met Val Ser Lys
            180                 185                 190

Trp Asp Ser Gly Val Pro Asp Arg Phe Ser Gly Ser Gly Ser Gly Thr
        195                 200                 205

Asp Phe Thr Leu Arg Ile Ser Arg Val Glu Ala Glu Asp Val Gly Val
    210                 215                 220

Tyr Tyr Cys Met Gln Ser Thr His Trp Pro Pro Thr Phe Gly Gly Gly
225                 230                 235                 240

Thr Lys Leu Glu Ile Lys Arg
                245
```

<210> SEQ ID NO 24
<211> LENGTH: 741
<212> TYPE: DNA
<213> ORGANISM: Artificial Sequence

```
<220> FEATURE:
<223> OTHER INFORMATION: 2H8, scFv, nucleotide sequence

<400> SEQUENCE: 24
gaggtgcagc tggtggagac tgggggcggc ttggtccagc ctgggggtc cctgagactc      60 tcctgtgcag cgtctggatt caccttcagt agctatggca tgcactgggt ccgccaggct     120
ccagggaagg gctggagtg gtctcagtt attagtggta gtggtgatag tacatactac      180
gcagagtccg tgaagggccg cttcaccatc tccagagaca tgccaggaa cacggtgtat     240 ctgcaaatga acagtctgag agccgaggac acggctgtat attattgtgc aagtggcatt     300
ttgactggtt atgtatttga ctattggggc aaagggacaa tggtcaccgt ctcgagtggt     360
ggaggcggtt caggcggagg tggttctggc ggtggcggat cggatgttgt gatgactcag     420
tctccactct ccctgcccgt cacccttgga cagccggcct ccatctcctg caggtctagt     480
caaagcctcg tatccaatga tggaaacacc tacttgaatt ggtttcagca gaggccaggc     540
caacctccaa ggcgcctaat ttatatggtt tctaagtggg actctggggt cccagacaga     600
ttcagcggca gtgggtcagg cactgatttc acactgagaa tcagcagggt ggaggctgag     660
gatgttgggg tttattactg catgcaaagt acacactggc tcccactttt cggcggaggg     720
accaagctgg agatcaaacg t                                                741

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
gcgaattccc catgaaagaa gcaaacatcc                                       30

<210> SEQ ID NO 26
<211> LENGTH: 35
<212> TYPE: DNA
<213> ORGANISM: Artificial Sequence
<220> FEATURE:
<223> OTHER INFORMATION: primer

<400> SEQUENCE: 26
ccgctcgagt tatcttcccc ttttaatggt caatg                                 35

<210> SEQ ID NO 27
<211> LENGTH: 330
<212> TYPE: DNA
<213> ORGANISM: Artificial Sequence
<220> FEATURE:
<223> OTHER INFORMATION: human proBDNF gene sequence

<400> SEQUENCE: 27
gcccccatga agaagcaaa catccgagga caaggtggct tggcctaccc aggtgtgcgg      60
acccatggga ctctggagag cgtgaatggg cccaaggcag gttcaagagg cttgacatca    120
ttggctgaca ctttcgaaca catgatagaa gagctgttgg atgaggacca gaaagttcgg    180
cccaatgaag aaaacaataa ggacgcagac ttgtacacgt ccagggtgat gctcagtagt    240
caagtgcctt tggagcctcc tcttctcttt ctgctggagg aatacaaaaa ttacctagat    300
gctgcaaaca tgtccatgag ggtccggcgc                                     330

<210> SEQ ID NO 28
```

<211> LENGTH: 36
<212> TYPE: DNA
<213> ORGANISM: Artificial Sequence
<220> FEATURE:
<223> OTHER INFORMATION: primer

<400> SEQUENCE: 28
gctggctagc acccatgaaa gaagcaaaca tccgag                           36

<210> SEQ ID NO 29
<211> LENGTH: 28
<212> TYPE: DNA
<213> ORGANISM: Artificial Sequence
<220> FEATURE:
<223> OTHER INFORMATION: primer

<400> SEQUENCE: 29
ccgctcgagg tggcgccgga ccctcatg                                    28

<210> SEQ ID NO 30
<211> LENGTH: 39
<212> TYPE: DNA
<213> ORGANISM: Artificial Sequence
<220> FEATURE:
<223> OTHER INFORMATION: primer

<400> SEQUENCE: 30
gcctttcctg gtttcctgtc tcaggtgcag ctggtggag                        39

<210> SEQ ID NO 31
<211> LENGTH: 38
<212> TYPE: DNA
<213> ORGANISM: Artificial Sequence
<220> FEATURE:
<223> OTHER INFORMATION: primer

<400> SEQUENCE: 31
atgggccctt ggtggaggca ctcgagacgg tgaccgtg                         38

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
ggctaactag agaacccact gc                                          22

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
agacaggaaa ccaggaaagg c                                           21

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
gcctccacca agggcccatc                                                  20

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
gacaatctta gcgcagaagt c                                                21

<210> SEQ ID NO 36
<211> LENGTH: 47
<212> TYPE: DNA
<213> ORGANISM: Artificial Sequence
<220> FEATURE:
<223> OTHER INFORMATION: primer

<400> SEQUENCE: 36
ctttggtttc caggtgcaag atgtgatgtt gtgatgactc agtctcc                    47

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
caccgtacgt ttgatctcca gcttgg                                           26

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
ggctaactag agaacccact gc                                               22

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
acatcttgca cctggaaacc aaag                                             24

<210> SEQ ID NO 40
<211> LENGTH: 56
<212> TYPE: PRT
<213> ORGANISM: Artificial Sequence
<220> FEATURE:
<223> OTHER INFORMATION: E1 peptide fragment

<400> SEQUENCE: 40

Pro Met Lys Glu Ala Asn Ile Arg Gly Gln Gly Gly Leu Ala Tyr Pro
1               5                   10                  15

Gly Val Arg Thr His Gly Thr Leu Glu Ser Val Asn Gly Pro Lys Ala
            20                  25                  30

Gly Ser Arg Gly Leu Thr Ser Leu Ala Asp Thr Phe Glu His Met Ile
            35                  40                  45

Glu Glu Leu Leu Asp Glu Asp Gln
    50                  55

<210> SEQ ID NO 41
<211> LENGTH: 54
<212> TYPE: PRT
<213> ORGANISM: Artificial Sequence
<220> FEATURE:
<223> OTHER INFORMATION: E2 peptide fragment

<400> SEQUENCE: 41

Lys Val Arg Pro Asn Glu Glu Asn Asn Lys Asp Ala Asp Leu Tyr Thr
1               5                   10                  15

Ser Arg Val Met Leu Ser Ser Gln Val Pro Leu Glu Pro Pro Leu Leu
            20                  25                  30

Phe Leu Leu Glu Glu Tyr Lys Asn Tyr Leu Asp Ala Ala Asn Met Ser
            35                  40                  45

Met Arg Val Arg Arg His
    50

<210> SEQ ID NO 42
<211> LENGTH: 37
<212> TYPE: PRT
<213> ORGANISM: Artificial Sequence
<220> FEATURE:
<223> OTHER INFORMATION: E3 peptide fragment

<400> SEQUENCE: 42

Pro Met Lys Glu Ala Asn Ile Arg Gly Gln Gly Gly Leu Ala Tyr Pro
1               5                   10                  15

Gly Val Arg Thr His Gly Thr Leu Glu Ser Val Asn Gly Pro Lys Ala
            20                  25                  30

Gly Ser Arg Gly Leu
        35

<210> SEQ ID NO 43
<211> LENGTH: 37
<212> TYPE: PRT
<213> ORGANISM: Artificial Sequence
<220> FEATURE:
<223> OTHER INFORMATION: E4 peptide fragment

<400> SEQUENCE: 43

Thr Ser Leu Ala Asp Thr Phe Glu His Met Ile Glu Glu Leu Leu Asp
1               5                   10                  15

Glu Asp Gln Lys Val Arg Pro Asn Glu Glu Asn Asn Lys Asp Ala Asp
            20                  25                  30

Leu Tyr Thr Ser Arg
        35

<210> SEQ ID NO 44
<211> LENGTH: 36
<212> TYPE: PRT
<213> ORGANISM: Artificial Sequence
<220> FEATURE:
<223> OTHER INFORMATION: E5 peptide fragment

<400> SEQUENCE: 44

Val Met Leu Ser Ser Gln Val Pro Leu Glu Pro Pro Leu Leu Phe Leu
1               5                   10                  15

```
Leu Glu Glu Tyr Lys Asn Tyr Leu Asp Ala Ala Asn Met Ser Met Arg
            20                  25                  30

Val Arg Arg His
        35

<210> SEQ ID NO 45
<211> LENGTH: 12
<212> TYPE: PRT
<213> ORGANISM: Artificial Sequence
<220> FEATURE:
<223> OTHER INFORMATION: VP peptide fragment

<400> SEQUENCE: 45

Val Met Leu Ser Ser Gln Val Pro Leu Glu Pro Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: LL peptide fragment

<400> SEQUENCE: 46

Leu Leu Phe Leu Leu Glu Glu Tyr Lys Asn Tyr Leu
1               5                   10

<210> SEQ ID NO 47
<211> LENGTH: 12
<212> TYPE: PRT
<213> ORGANISM: Artificial Sequence
<220> FEATURE:
<223> OTHER INFORMATION: DH peptide fragment

<400> SEQUENCE: 47

Asp Ala Ala Asn Met Ser Met Arg Val Arg Arg His
1               5                   10
```